United States Patent
Tse et al.

(10) Patent No.: US 9,747,257 B2
(45) Date of Patent: Aug. 29, 2017

(54) UPDATING DOCUMENT PREVIEWS OF EMBEDDED FILES

(75) Inventors: David Tse, Kirkland, WA (US); Omer Atay, Federal Way, WA (US)

(73) Assignee: MICROSOFT TECHNOLOGY LICENSING, LLC, Redmond, WA (US)

(*) Notice: Subject to any disclaimer, the term of this patent is extended or adjusted under 35 U.S.C. 154(b) by 1150 days.

(21) Appl. No.: 13/342,117

(22) Filed: Jan. 2, 2012

(65) Prior Publication Data

US 2013/0174032 A1    Jul. 4, 2013

(51) Int. Cl.
| | |
|---|---|
| G06F 17/00 | (2006.01) |
| G06F 17/21 | (2006.01) |
| G06F 17/24 | (2006.01) |
| G06F 19/24 | (2011.01) |
| G06F 17/22 | (2006.01) |
| G06F 17/30 | (2006.01) |
| G06F 19/00 | (2011.01) |
| G06F 3/0481 | (2013.01) |

(52) U.S. Cl.
CPC ........ G06F 17/212 (2013.01); G06F 17/2235 (2013.01); G06F 17/24 (2013.01); *G06F 3/0481* (2013.01); *G06F 17/211* (2013.01); *G06F 17/2247* (2013.01); *G06F 17/3002* (2013.01); *G06F 17/30126* (2013.01); *G06F 19/24* (2013.01); *G06F 19/707* (2013.01)

(58) Field of Classification Search
CPC .... G06F 17/122; G06F 17/24; G06F 17/2235; G06F 19/24; G06F 19/707; G06F 17/30383; G06F 17/30002; G06F 17/2247; G06F 17/211–17/212; G06F 17/30125; G06F 17/246; G06F 3/0481; G06F 3/0483
USPC ......................... 715/273, 753, 776
See application file for complete search history.

(56) References Cited

U.S. PATENT DOCUMENTS

| | | |
|---|---|---|
| 7,490,288 B2 | 2/2009 | Undasan |
| 7,528,847 B2 | 5/2009 | Braun et al. |
| 2006/0161841 A1 | 7/2006 | Horiuchi et al. |
| 2006/0271574 A1 | 11/2006 | Villaron et al. |
| 2007/0195959 A1* | 8/2007 | Clarke ...................... H04L 9/12 380/278 |
| 2007/0266342 A1* | 11/2007 | Chang et al. ................. 715/810 |
| 2008/0115069 A1* | 5/2008 | Veselova ....................... 715/760 |
| 2008/0244442 A1* | 10/2008 | Veselova ............... G06F 9/4443 715/781 |
| 2008/0256113 A1* | 10/2008 | Rasmussen ......... G06F 17/2205 |
| 2010/0312822 A1 | 12/2010 | Howell et al. |

(Continued)

OTHER PUBLICATIONS

Walkenbach et al., ("Microsoft Office 2010 Bible" Published 2010 by Wiley Publishing [22 Pages].*

(Continued)

*Primary Examiner* — Quoc A Tran
(74) *Attorney, Agent, or Firm* — Christopher J. Volkmann; Kelly, Holt & Christenson, PLLC

(57) ABSTRACT

When a multi-page document is embedded in a notebook system, a preview object is generated for pages of the embedded document. The preview objects are displayed in the notebook, and when a user modifies the document underlying the preview objects, to change a relationship between the preview objects, the preview objects are synchronized with the underlying document to reflect those modifications.

20 Claims, 21 Drawing Sheets

(56) References Cited

U.S. PATENT DOCUMENTS

2012/0084644 A1* 4/2012 Robert .............. G06F 17/30126
715/255
2013/0252225 A1* 9/2013 Hayashi et al. .............. 434/362

OTHER PUBLICATIONS

Oldenburg ["Using Microsoft Office 2010" Published Sep. 6, 2011 by QUE—Chapter 12 [52 pages].*
Oldenburg ["Using Microsoft Office 2010" Published Sep. 6, 2011 by QUE—Chapter 5 [39 pages].*
Oldenburg ["Using Microsoft Office 2010" Published Sep. 6, 2011 by QUE—Chapter 12—52 pages and Chapter 5—39 pages.*
"Preview Attachments", Retrieved at <<http://office.microsoft.com/en-us/outlook-help/preview-attachments-HA010236673.aspx>>, Retrieved Date: Nov. 23, 2011, pp. 1-3.
"Troubleshoot SkyDrive Sync Errors in OneNote 2010", Retrieved at <<http://www.onenotehelp.com/2010/07/17/troubleshoot-skydrive-sync-errors-in-onenote-2010/>>, Retrieved Date: Nov. 22, 2011, pp. 1-7.
Escapa, Daniel, "Overview of OneNote 2010—What's New for You", Retrieved at <<http://blogs.msdn.com/b/descapa/archive/2009/07/15/overview-of-onenote-2010-what-s-new-for-you.aspx>>, Retrieved Date: Nov. 22, 2011, pp. 1-7.

* cited by examiner

UPDATING DOCUMENT PREVIEWS OF EMBEDDED FILES

BACKGROUND

Some systems currently allow a plurality of different users to collaborate on developing content in a knowledge base. For instance, in some notebook systems, a notebook application maintains a plurality of different notebooks. Each notebook can be divided into a plurality of different sections, and each section may have one or more pages. The pages can have content either provided thereon, or embedded therein. For example, the pages can simply have text written on them as a word processing document, or they can have embedded drawing files, audio files, video files, spreadsheet documents, and slide presentation documents, among other things.

In some notebook systems, the page where a document is embedded has an icon or other display element representing the embedded document. When a user actuates the icon or display element (such as by double clicking it, or selecting it and pressing enter, or otherwise) notebook system can launch the underlying application that was used to author or display the embedded document.

The discussion above is merely provided for general background information and is not intended to be used as an aid in determining the scope of the claimed subject matter.

SUMMARY

When a multi-page document is embedded in a notebook system, a preview object is generated for pages of the embedded document. The preview objects are displayed in the notebook, and when a user modifies the document underlying the preview objects, to change a relationship between the preview objects, the preview objects are synchronized with the underlying document to reflect those modifications.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the background.

DETAILED DESCRIPTION

Figure 1:
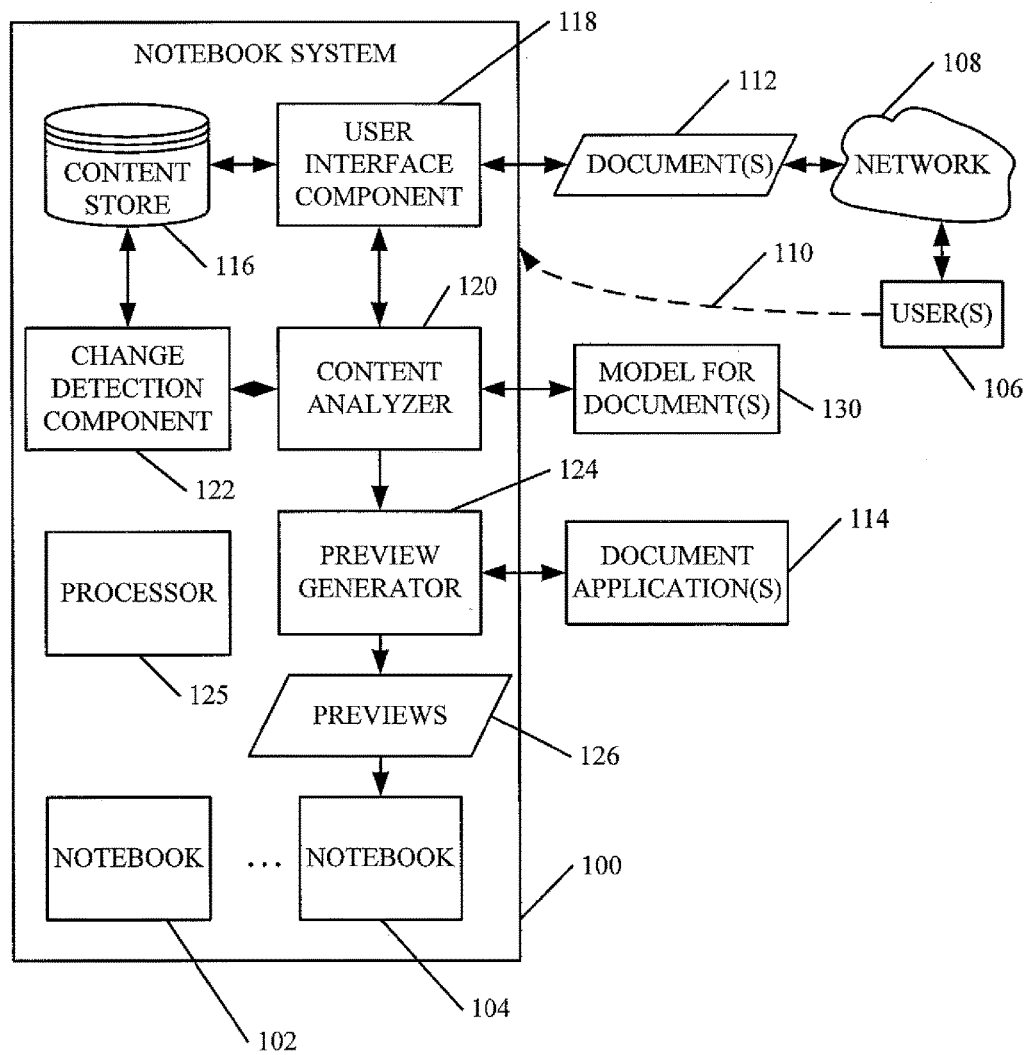
FIG. 1 is a block diagram of one embodiment of a notebook system.

FIG. 1 shows a block diagram of one illustrative notebook system 100 that runs a notebook application that supports a plurality of notebooks 102 and 104. A plurality of users 106 can illustratively collaborate on developing content in notebooks 102-104, by accessing notebook system 100, through network 108. In one embodiment, network 108 is a wide area network (such as the internet) but it could be a local area network, or users 106 could access notebook system 100 directly, as indicated by dashed arrow 110. In one embodiment, and as is discussed in greater detail below, user 106 can provide one or more documents, 112 that are to be embedded in one of the notebooks 102-104.

As used herein, the term document will include a multipage collection of content. For instance, a document may be a multi-page word processing document, a multi-page spreadsheet document, a multi-page slide presentation document, a multi-page drawing document, or another similar document.

Each of the documents 112 provided by users 106 is generated or authored using a document application 114. In FIG. 1, notebook system 100 is shown having access to those document applications 114 as well.

FIG. 1 also shows that notebook system 100 includes a content store 116, a user interface component 118, content analyzer 120, change detection component 122, preview generator 124 and processor 125. Processor 125 is illustratively a computer processor that includes associated timing circuitry and memory (not shown). Processor 125 can be coupled to, and activated by, the various components 100 to facilitate the functionality of those components.

The operation of notebook system 100 in generating previews for documents 112 is described in greater detail below. Briefly, in one embodiment, when the user 106 provides a document 112 to notebook system 100, this can be done through a user interface generated by user interface component 118, that includes a user input mechanism thereon. For instance, the user may be able to drag and drop a document 112 from one location into a notebook (such as notebook 104) on a user interface display in order to embed the document 112 at a given location in notebook 104. Of course, the user can illustratively use gestures on a touch sensitive display or a pointing device or other hardware or software user input mechanism.

In any case, when user 106 provides a document 112 to be embedded in a notebook 104, analyzer 120 illustratively analyzes the content of document 112. In doing so, it can make use of a model for the document 130, where one is available. Content analyzer 120 analyzes document 112 to identify embedded objects corresponding to each page in document 112 and provides those objects to preview generator 124, which generates previews 126 that are provided to notebook 104. One preview 126 illustratively corresponds to each page of the document 112.

It may happen that user 106 changes the underlying document for which the previews 126 were generated. When that happens, change detection component 122 detects changes based on the previous previews 126 generated for that document (which were also stored in content store 116) and the currently available preview objects. When a change has occurred, content analyzer 120 again uses preview generator 124 to generate previews for the modified document, and the modified previews are stored in notebook 104.

Figure 2:
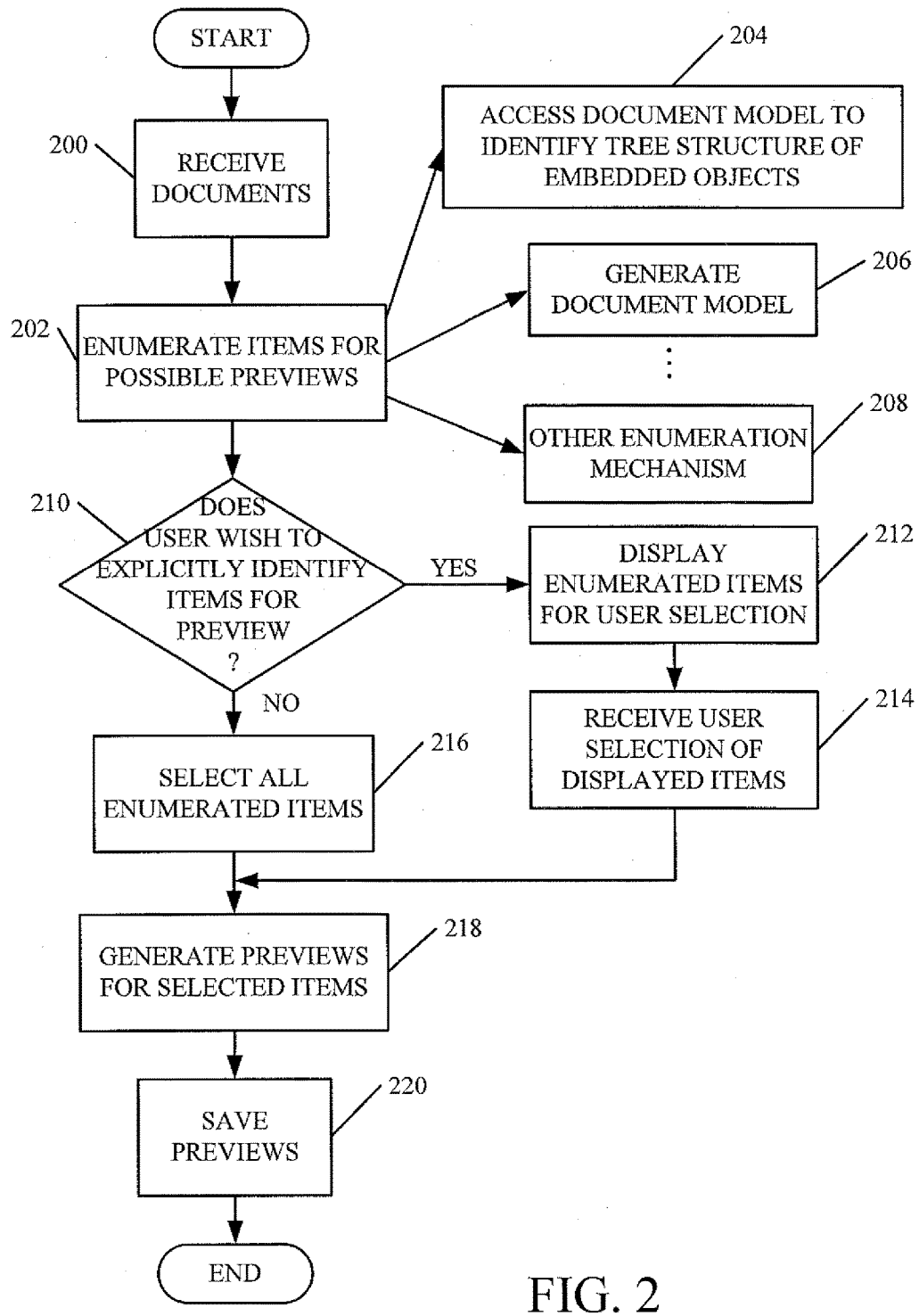
FIG. 2 is a flow diagram illustrating one embodiment of the operation of the system shown in FIG. 1.

FIG. 2 is a flow diagram illustrating one embodiment of the operation of system 100 shown in FIG. 1 in generating previews for a document 112 to be embedded in a notebook 104. User interface component 118 illustratively first displays a user interface display that allows user 106 to input document 112 into notebook system 100. This can be done in a wide variety of different ways (as described below with respect to FIGS. 2A-2H) and is indicated by block 200 in FIG. 2.

Figure 2A:
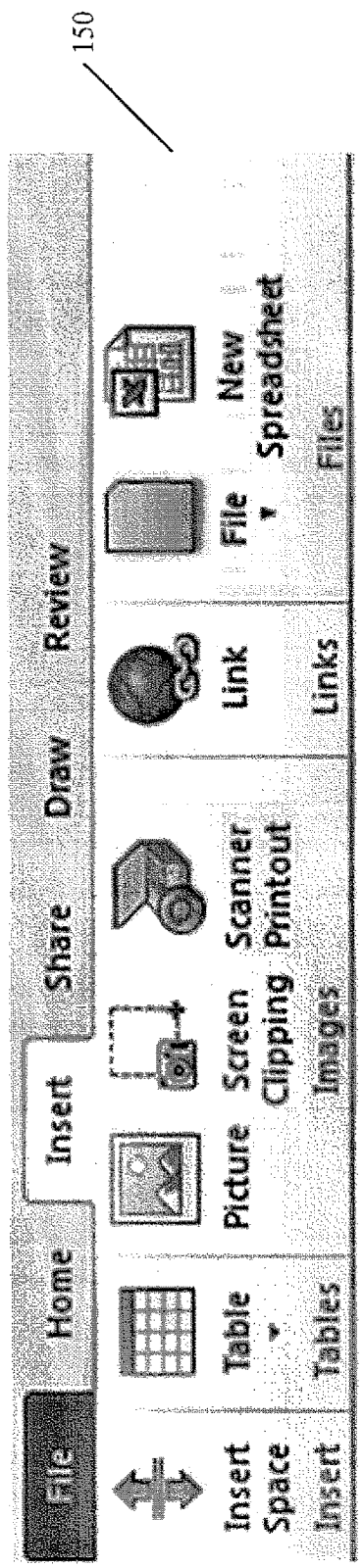
FIGS. 2A-2H illustrate exemplary user interface displays.
Figure 2B:
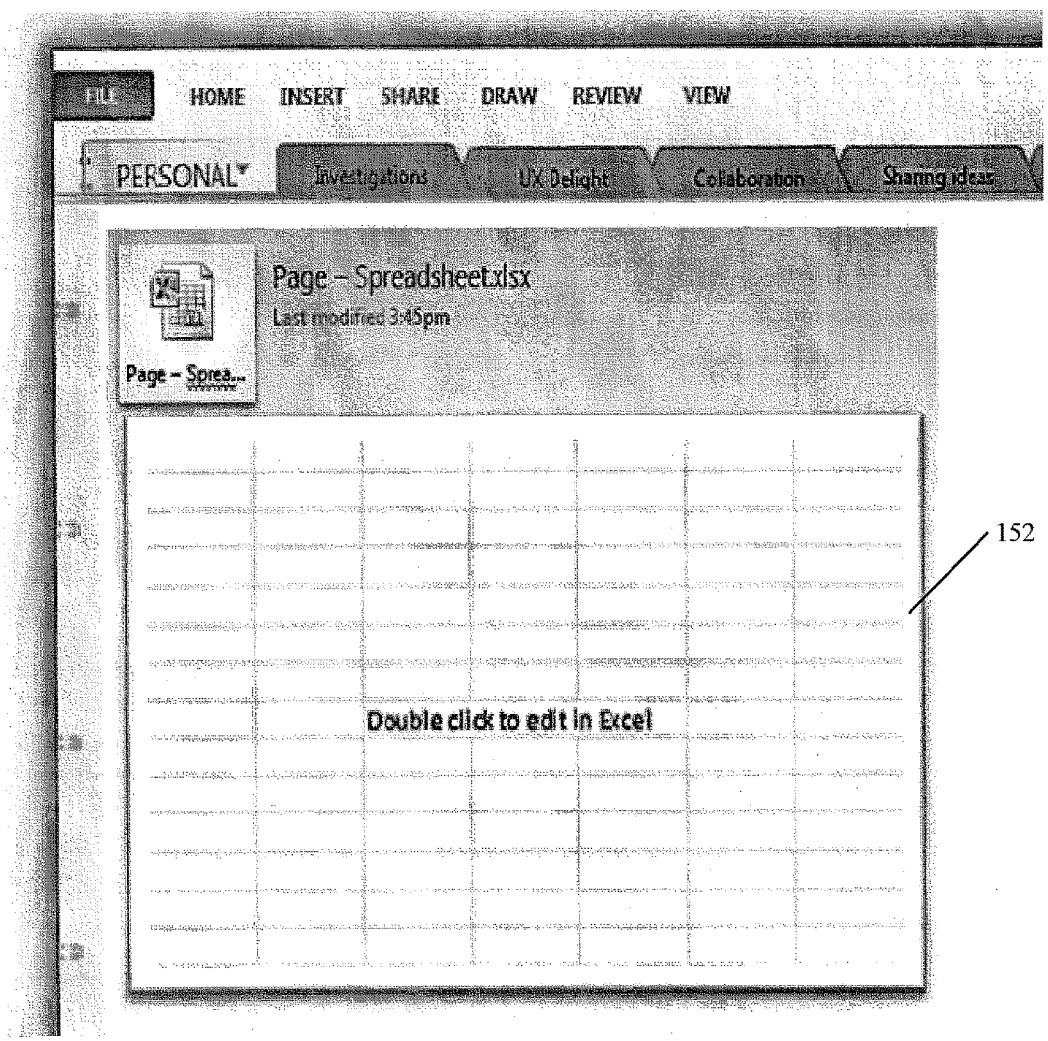

For instance, FIG. 2A shows one illustrative user interface display of a toolbar 150 in a ribbon that is displayed when a "Insert" tab is selected by a user on the user interface display. The various portions of toolbar 150 allow user 106 to input document 112 in a variety of different ways. For instance, when the user 106 selects the "New Spreadsheet" button on ribbon 150, user interface component 118 illustratively generates a user interface display such as that shown in FIG. 2B. In order to do this, notebook system 100 first creates a new spreadsheet file and inserts it on the page in the notebook 104 to which the user has navigated, and displays a live object showing the first sheet of the spreadsheet, as indicated at 152 in FIG. 2B. In order to do this, notebook system 100 creates an empty spreadsheet file and then launches the spreadsheet application (from document applications 114). This allows user 106 to effectively input a spreadsheet document 112 into a notebook 104.

Figure 2C:
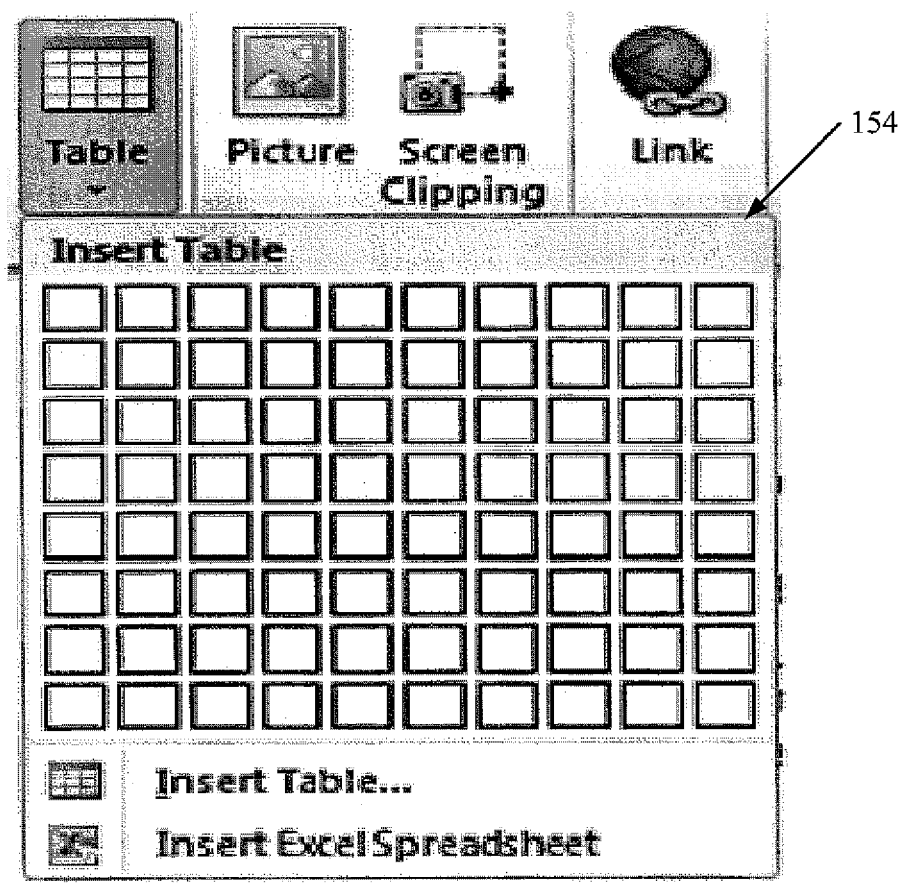
Figure 2D:
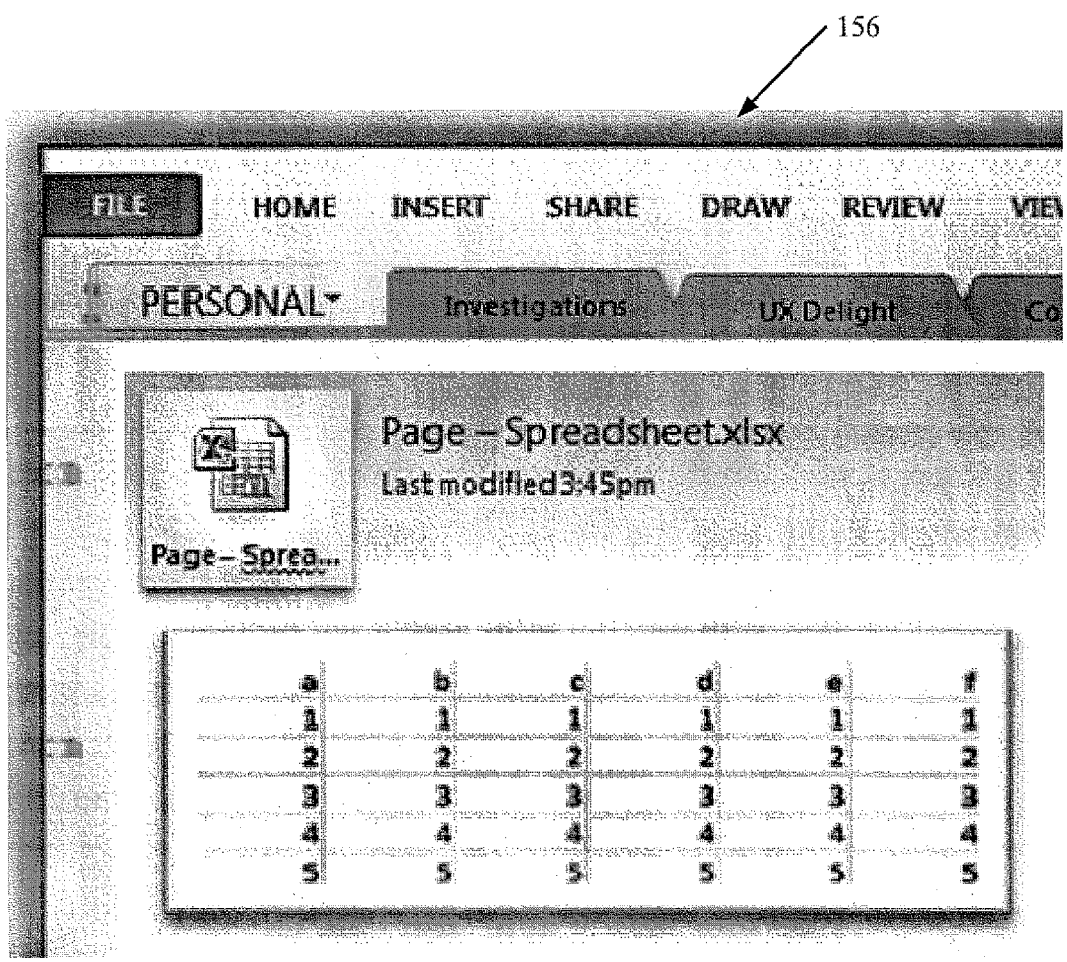

FIG. 2C shows that in one illustrative embodiment, user interface display 154 is generated when the user selects the Table button on ribbon 150 in FIG. 2A. In that case, user 106 can insert either a spreadsheet or an individual table.

Where the user elects to insert a table, instead of an entire spreadsheet, user interface component 118 illustratively generates a user interface display such as display 156 in FIG. 2D. It will be assumed that the user has started with content that has an existing table. It can be seen that when the user selects the "Insert Table" button, notebook system 100 first opens a new spreadsheet file and exports the identified table into the new spreadsheet file. In one embodiment, notebook system 100 inserts the spreadsheet and sets it to display the entire spreadsheet when notebook 104 is opened. It then launches the spreadsheet application 114 so that the spreadsheet is open and editable by user 106. Alternatively, the user can use another option, such as a "covert to spreadsheet" option (not shown). When that option is used, the system converts a selected table into an embedded spreadsheet with previews. Other options can be used as well.

Figure 2E:
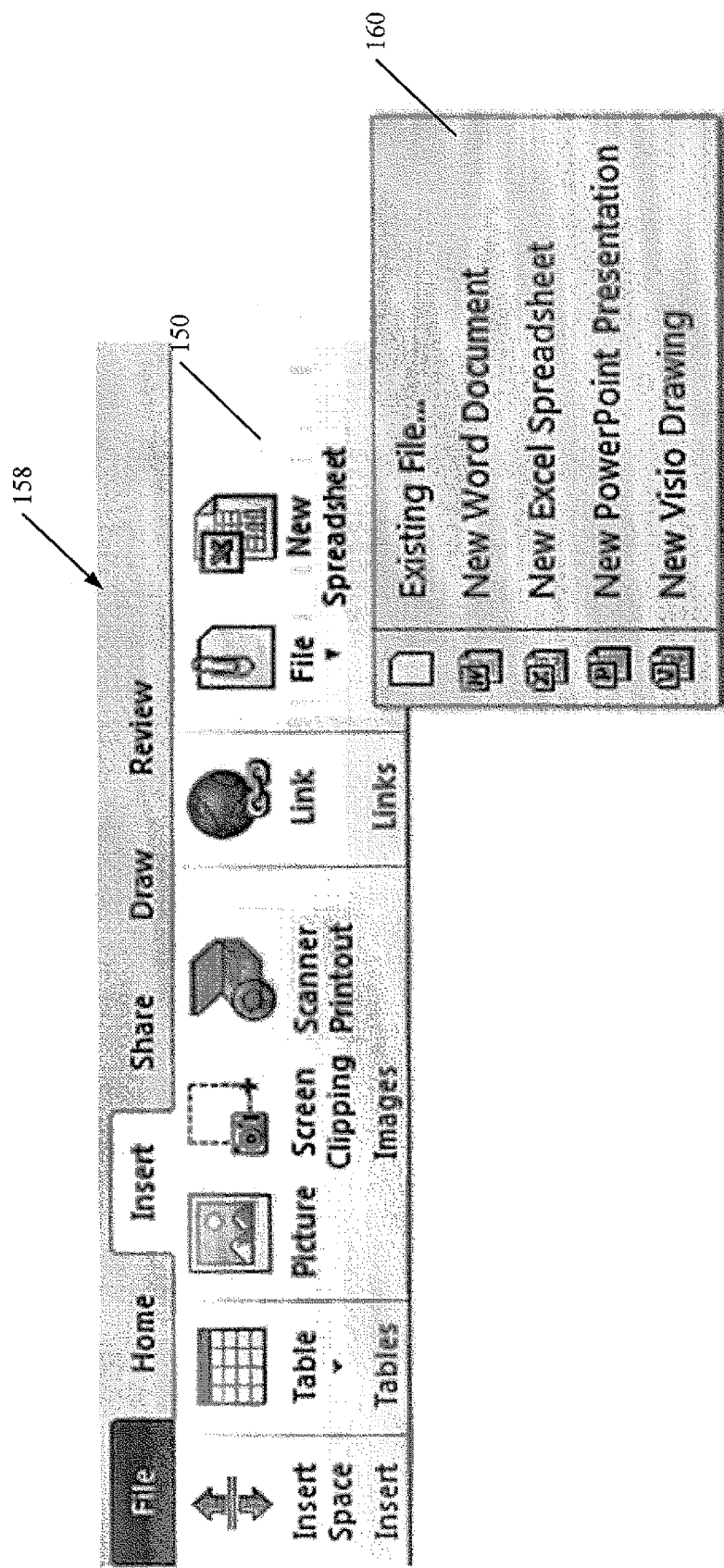
Figure 2F:
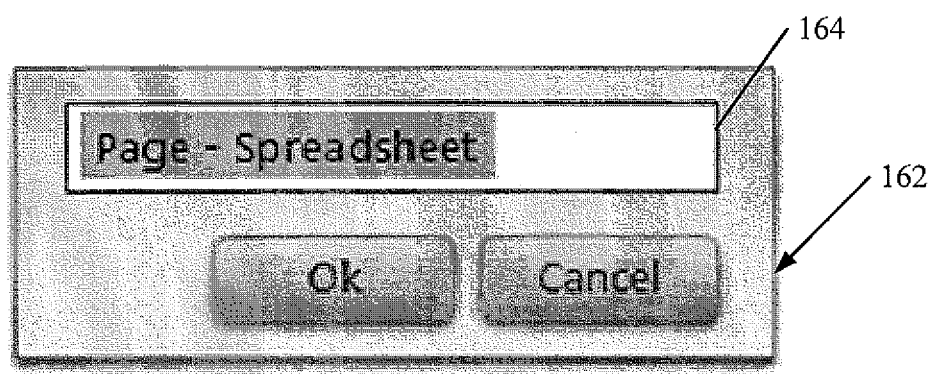

FIG. 2E shows that user interface component 118 can generate yet another user interface display 158 when the user actuates the "File" button on ribbon 150. In one embodiment, display 158 will include a dropdown menu 160 that allows the user to create a new type of document for embedding into notebook 104. When the user selects one of the entries in dropdown menu 160, notebook system 100 illustratively creates an appropriate file corresponding to the selected file type and enables user 106 to name or rename that file if desired. For instance, by right clicking on the file, in one embodiment, user interface component 118 will generate a user interface display such as display 162 shown in FIG. 2F. Display 162 provides a textbox 164 that allows the user to type in a name that will be given to the embedded document.

Figure 2G:
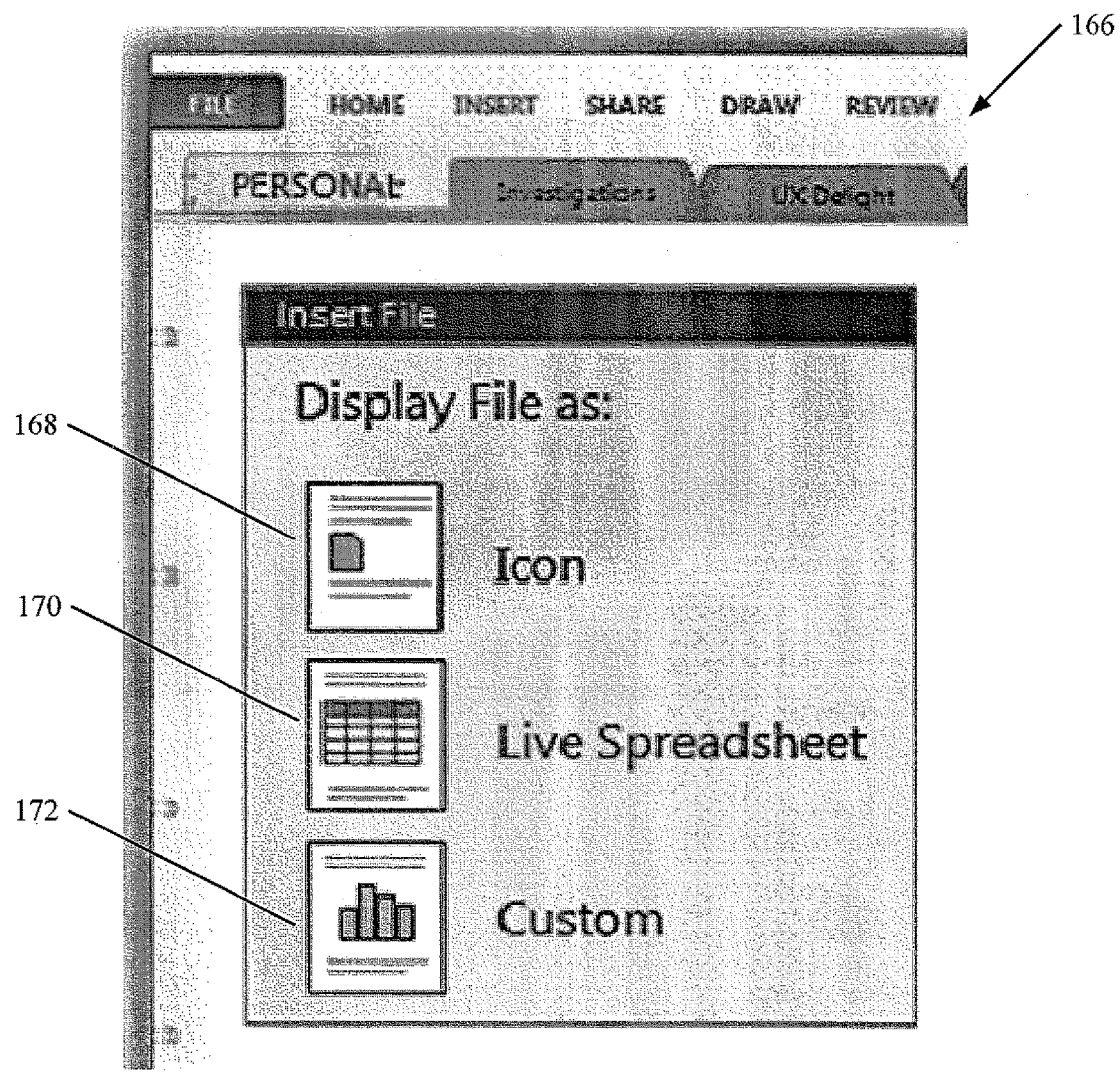

FIG. 2G shows yet another embodiment in which user interface component 118 generates a user interface display that allows user 106 to embed document 112 by using drag and drop operations. For instance, from user interface display 158 shown in FIG. 2E, if the user selects the "Existing File" button in dropdown menu 160, the user is allowed to navigate to a set of displayed files that can be dragged and dropped onto another portion of the user interface display corresponding to notebook 104. FIG. 2G shows a user interface display 166 that can be generated by user interface component 118 when that occurs. In the example shown in FIG. 2G, it is assumed that the file that has been dragged onto notebook 104 and dropped there is a spreadsheet file. If the user selects the icon button 168 from display 166, this causes notebook system 100 to embed the selected spreadsheet file onto the page in notebook 104 where the file was dragged and dropped. If the user selects the "Live Spreadsheet" button 170, notebook system 100 will embed the entire spreadsheet file on the page. A preview will be generated for each page in the document. If, on the other hand, the user selects the "Custom" button 172, then notebook system 100 will still embed the entire document, but will generate another user interface display that allows the user to select certain portions of the file for which previews will be generated.

Figure 2H:
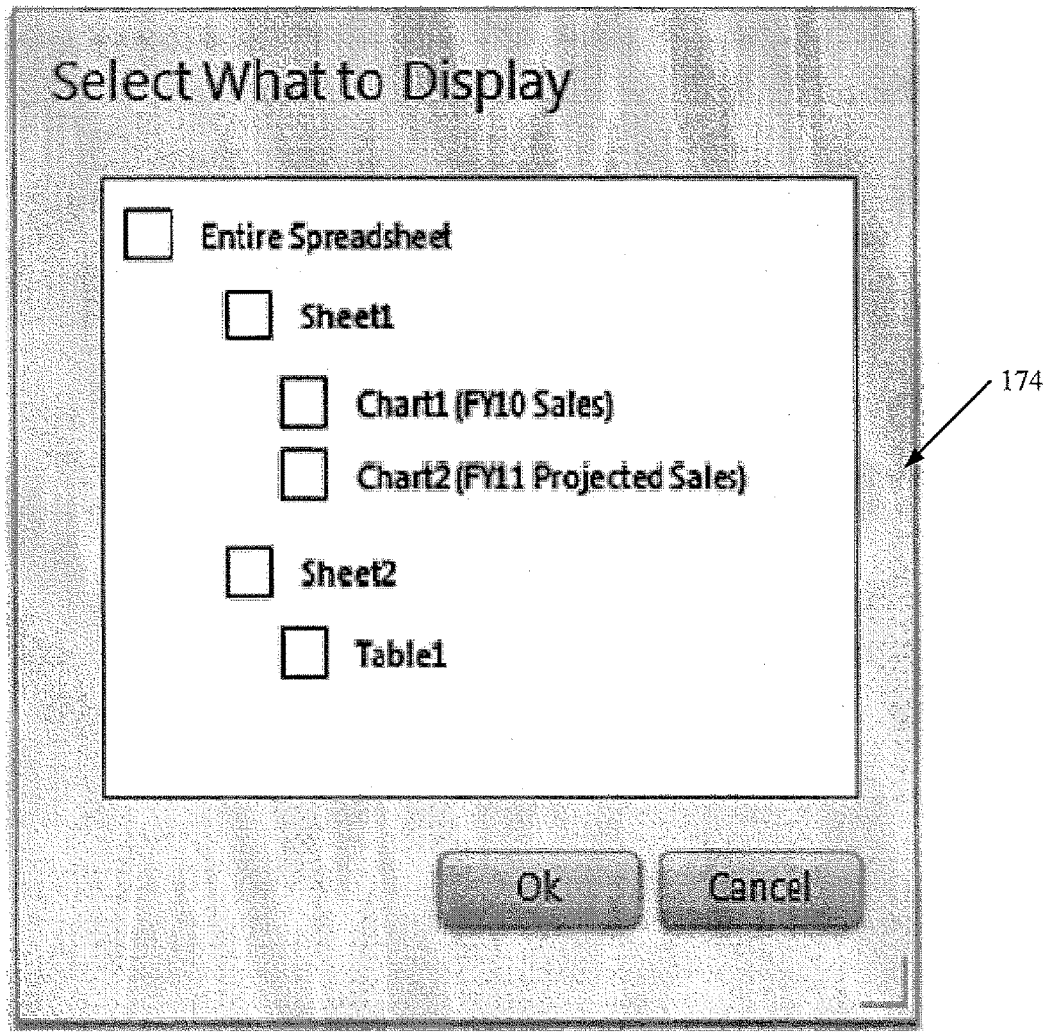

FIG. 2H shows one illustrative user interface display 174 that allows user 106 to choose certain portions of the spreadsheet file dragged into notebook 104 as discussed above with respect to FIG. 2G. Basically, the file (or document) that was dragged and dropped onto notebook 104 is provided to content analyzer 120. Content analyzer analyzes the content of the document and displays that content in display 174, for user selection. When it is displayed, the user can select certain portions of the content for which previews are to be generated and displayed at the given location in notebook 104, and those items will be identified. While the entire document will be embedded, previews are only generated for each portion of the document selected when the "Custom" button 172 is actuated. The generated previews are shown on the given page on notebook 104.

In order to generate the user interface display 174 which allows user 106 to select, in a customized way, certain portions of document 112 to be previewed, content analyzer 120 enumerates all of the items in document 112 for which a preview may be generated. This is indicated by block 202 in FIG. 2. This can be done in a variety of different ways.

In accordance with one embodiment, content analyzer 120 accesses a model 130 for document 112 and uses the model to scan document 112 to identify certain portions for which a preview can be displayed. In performing this type of operation, content analyzer 120 looks for a tree structure of embeddable objects within document 112. This will be done in accordance with object model 130 for the given document and it will vary based on the type of document application 114 used to author the embedded document. In the embodiment shown in FIG. 2H, it can be seen that content analyzer 120 has scanned the spreadsheet that is dragged and dropped into notebook 104 and identified that the spreadsheet has two sheets identified as "sheet one" and "sheet two" on the display 174. Content analyzer 120 has also identified that "sheet one" includes two charts labeled "chart 1" and "chart 2". Content analyzer 120 has also identified a table "Table 1" on sheet two of document 112.

It can also be seen that user interface component 118 has generated display 174 such that each of the items on the hierarchical tree on display 124 has a check box. The check boxes can be selected by the user to include those adjacent items to be embedded in notebook 104. Checking a given node in the hierarchical tree structure causes notebook system 100 to automatically check all of the subnodes (or child nodes) that are dependent on that node. For instance, if the user checks "entire spreadsheet" then all of the items on display 174 will be checked. Alternatively, if the user checks "sheet one" then both charts on sheet one will be selected as well. In the alternative, the user can select either chart one or chart two individually.

The tree structure may also be a flat tree structure. For instance, if document 112 is simply a word processing document, then the object model 130 corresponding to that document illustratively reveals that the tree structure is composed of a flat structure, one node corresponding to each page in the document, with all nodes on the same hierarchical level. However, a page may have another embedded document which can be identified as well. In that case, the tree structure is not flat, but the embedded document is a child node of the page node corresponding to the page of the word processing document on which it is embedded.

Similarly, where document 112 is a drawing document, or a slide presentation document, the object model 130 corresponding to document 112 may identify a flat tree structure where every sheet of drawings in the drawing document, or every slide in the slide presentation, corresponds to a node in a flat tree structure. It will be noted, of course, that those nodes may have other embedded documents in them as well. For instance, a slide in a slide presentation may have a spreadsheet embedded therein. In that case, content analyzer 120 may illustratively access two different object models 130, one (a slide presentation application) for the slide presentation itself, and one (a spreadsheet application) for the embedded spreadsheet document. This type of iterative content analysis is contemplated herein. In any case, accessing document model 130 to identify a tree structure of previewable, embeddable objects is indicated by block 204 in FIG. 2.

In another embodiment, the user can select, through an appropriate user interface generated by user interface component 118, to print a document to notebook system 100. In that case, one printable version is an XPS file, although other file types can be used as well. This generates a series of pages for the printable version of document 112, and each page can be identified by content analyzer 120 as an embeddable object. Generating an XPS file is indicated by block 206 in FIG. 2. It will be noted, of course, that content analyzer 120 can use other enumeration mechanisms for enumerating the previewable objects in the document 112 that is to be embedded in notebook 104. This is indicated by block 208 in FIG. 2.

Having enumerated and displayed the previewable objects to user 106, through an appropriate user interface, content analyzer 120 then determines whether the user wishes to explicitly identify items for which previews are to be generated or whether preview generator 124 is simply to generate previews for all possible items enumerated by content analyzer 120. This is indicated by block 210 in FIG. 2. If the user wishes to customize those previewable objects, then user interface component 118 generates the user interface 174 shown in FIG. 2H, and the user selects (from the displayed items) those for which a preview object is to be generated. This is indicated by blocks 212 and 214 in FIG. 2.

If, at block 210, it is determined that the user wishes to have preview objects generated for all enumerated items, and embedded in notebook 104, then all of the items enumerated at block 102 are selected by content analyzer 120. This is indicated at block 216 in FIG. 2.

In any case, all of the enumerated items, that have been selected to have a preview generated therefore, are provided to preview generator 124. Preview generator 124 generates previews 126 for the selected items. This is indicated by block 218 in FIG. 2. The previews 126 are then stored in content store 116, at the desired location in notebook 104. Saving the previews is indicated by block 220 in FIG. 2.

In generating the previews, preview generator 124 may illustratively identify the size of the preview to be generated. For instance, where the underlying document for which a preview is to be generated is a page of a spreadsheet document, preview generator 124 may identify only cells that contain content on a given page of the spreadsheet document. Preview generator 124 can then illustratively limit the size of the preview to show only the cells where content has been entered. Other ways of determining size can be used as well, depending upon the underlying application used to author the document.

At this point, every time a user 106 accesses notebook 104, and navigates to the page where the objects have been embedded, the previews for the embedded documents are displayed to the user. If the user actuates one of those embedded previews, notebook system 100 launches the underlying document application 114 that was used to author the document and navigates the user to the page in the document corresponding to the item that has been selected. For instance, if the embedded document is a word processing document, and the user has selected a preview object corresponding to a page in the embedded word processing document, then notebook system 100 launches the word processing application 114 used to author the word processing document and navigates the user to the page corresponding to the selected preview.

It should also be noted that, if the user changes the relationship between the embedded previews, or modifies the underlying documents so the previews should be changed, notebook system 100 automatically detects this and synchronizes the generated previews 126 with the underlying document, or with the changes to the relationship between the previews, or both.

Figure 3:
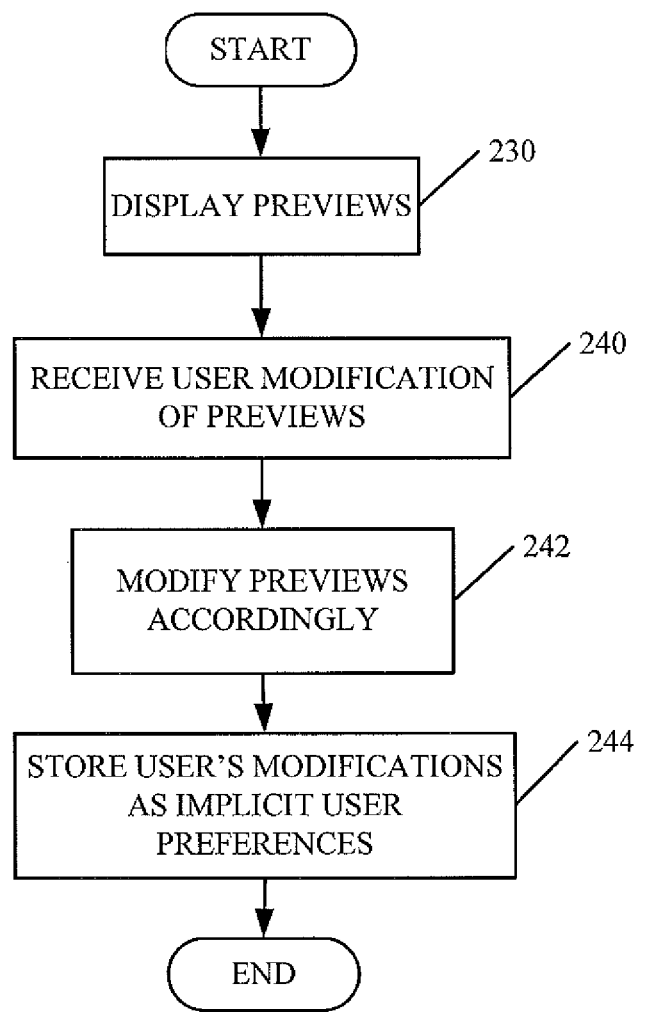
FIG. 3 is a flow diagram illustrating one embodiment of the operation of the system shown in FIG. 1 in setting implicit user preferences.

FIG. 3 is a flow diagram illustrating this type of synchronization where the user simply changes or edits the preview objects displayed in notebook 104. This can happen, for instance, if a user initially selects to have all enumerated items in a document embedded and have preview objects generated for each of them. However, when the user then goes to look at that page in notebook 104, the user may notice that he or she does not need to have all of those items (e.g., pages) from the underlying document embedded in notebook 104, and the user may simply wish to delete some of the embedded items for which previews have been generated. Notebook system 100 allows the user to easily make these changes, and the changes are detected by change detection component 122 so that preview generator 124 modifies the generated previews corresponding to the embedded document so that they are synchronized with the changes made by the user. FIG. 3 discusses this in more detail.

First, when a user 106 opens notebook 104 and navigates to the page where the document has been embedded, user interface component 118 displays the previews 126 that were previously generated for the embedded document, and stored in content store 116. This is indicated by block 230 in FIG. 3.

Figure 3A:
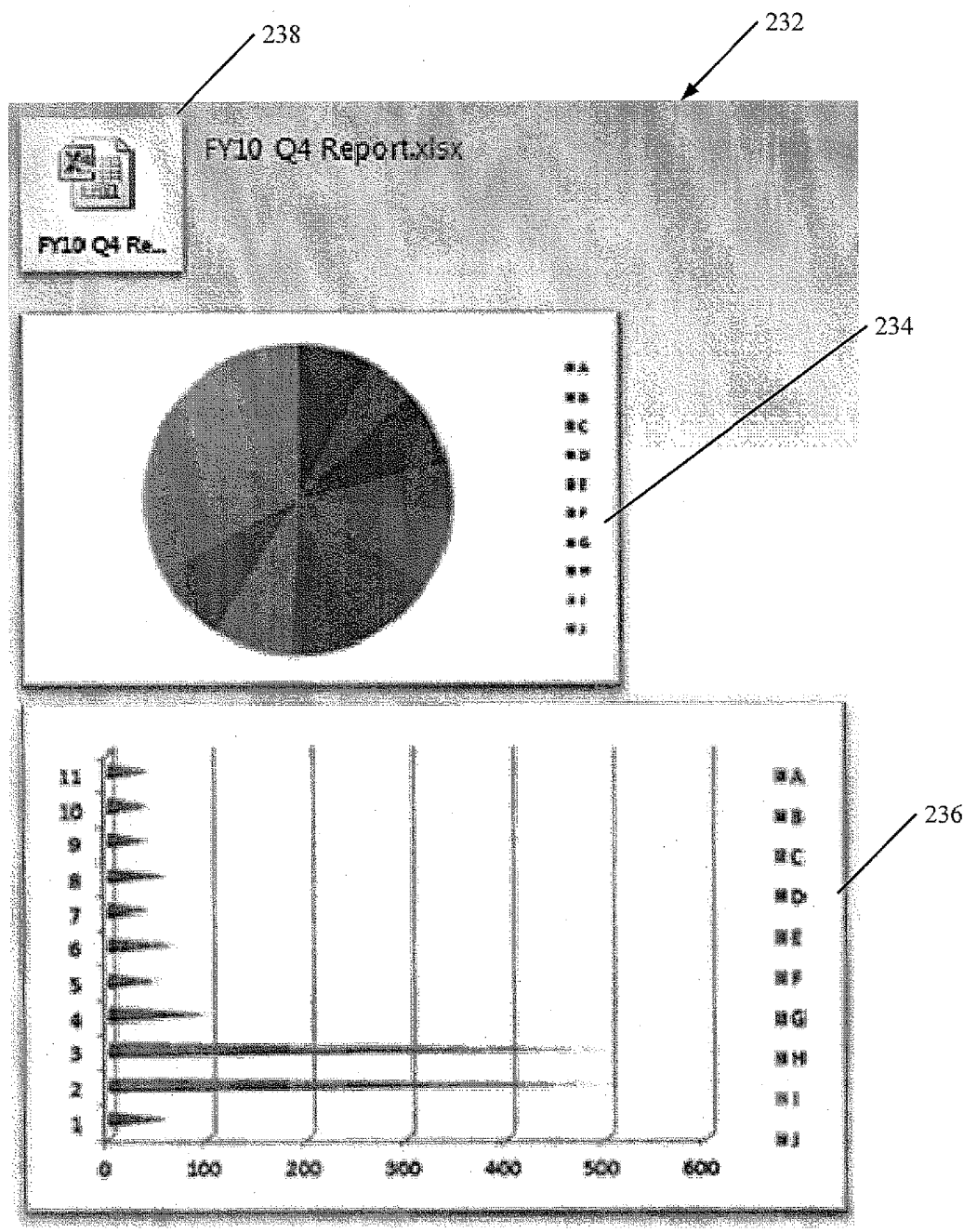
FIG. 3A shows an illustrative user interface display.

FIG. 3A shows one illustrative user interface 232 that is generated by user interface component 118 showing previews 234 and 236 for an embedded spreadsheet document represented by icon 238. Notebook system 100 may then receive, illustratively through manipulation of the user interface generated by user interface component 118, a user modification of the previews. This is indicated by block 240 in FIG. 3. By way of example, assume that the user no longer wishes to have the chart represented by preview 234 embedded in notebook 104. The user can simply select that preview and delete it. In that case, the only preview generated for the spreadsheet represented by icon 238 is the preview 236. Notebook system 100 thus deletes preview 234 from the display generated by user interface component 118. Modifying the previews in accordance with the instructions of user 106 is indicated by block 242 in FIG. 3.

When the user navigates away from that page of notebook 104, or when the user explicitly saves that page of notebook 104, change detection component 122 detects the user modification to the displayed previews 126 corresponding to the document represented by icon 238. This change is stored by change detection component 122 in content store 116 as one of the user's implicit preferences. This is indicated by block 244 in FIG. 3. This means that, even if the underlying document represented by icon 238 is changed so that the page corresponding to preview 234 is modified, that preview will not be generated the next time user 106 accesses the given page in notebook 104. Instead, when the user navigates to that page where the document is embedded in notebook 104, the previews 126 retrieved for that document from content store 116 will only include preview 236 shown in FIG. 3A. That is because notebook system 100 will know that the user previously deleted preview 234 and does not wish to have that item of the underlying document previewed in notebook 104 any longer.

The same type of processing is performed if the user performs any other modifications to the displayed previews. For instance, if the user rearranges the order of the displayed previews from within notebook 104, even though the user does not modify the content of the displayed previews individually, the change in relationship among the displayed previews is detected by change detection component 122, and stored in content store 116. Therefore, the next time that the user navigates to that page of document 104, the previews of the embedded items will be displayed in the new order, as last modified by the user. Of course, other user modifications to the previews themselves, or to the relationship between the previews, is detected and stored as an implicit user preference for generating previews next time the user navigates to notebook 104.

Figure 4:
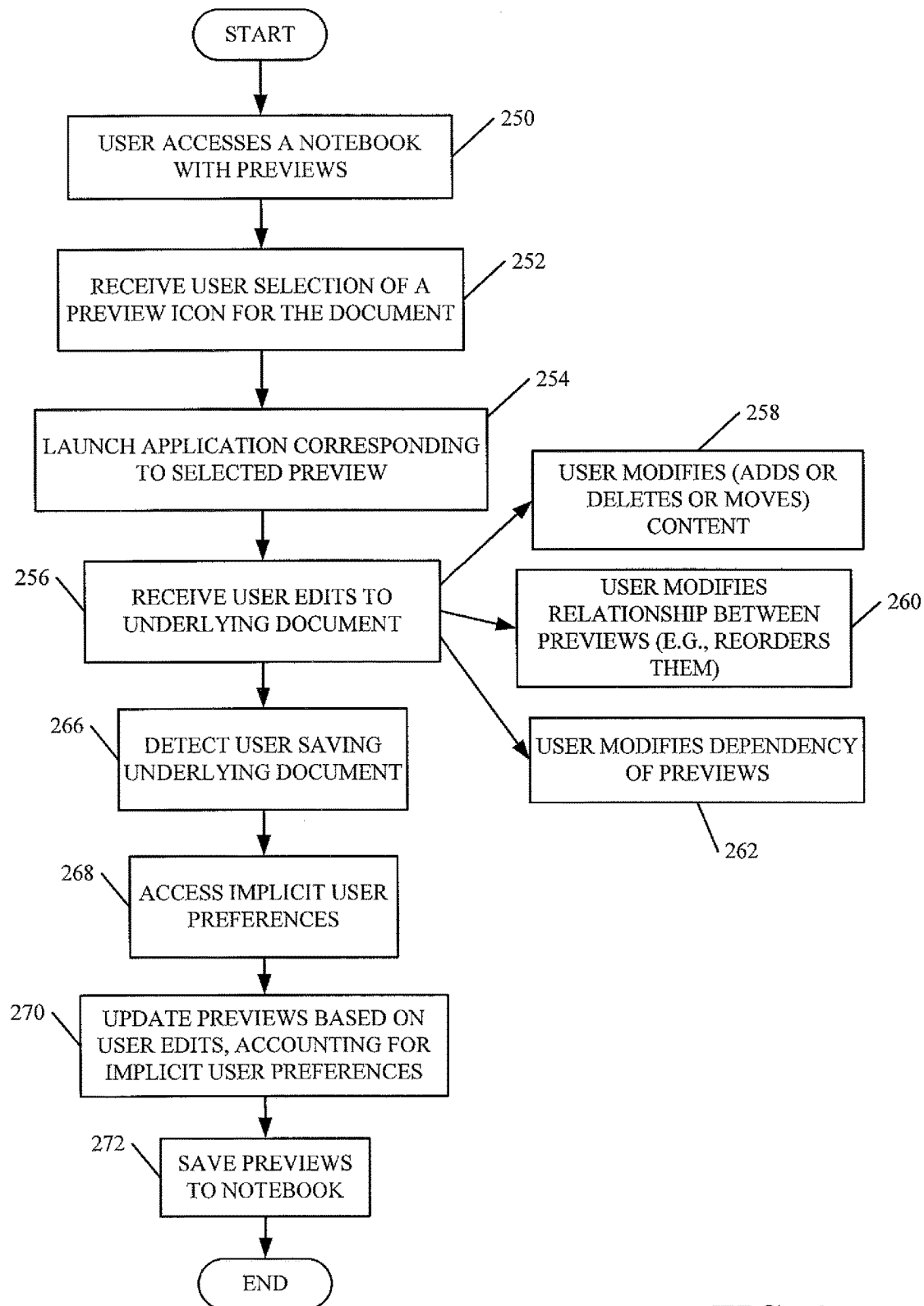
FIG. 4 is a flow diagram illustrating one embodiment of the operation of the system shown in FIG. 1 in synchronizing previews of a document with user modifications to the document.

Instead of modifying just the previews in notebook 104, user 106 may modify the underlying document for which previews 126 have been generated. For instance, assume that user 106 navigates to the page in notebook 104 that contains the embedded document. Then, assume that the user has clicked on either one of the previews 126, or the icon representing the embedded document. In that case, notebook system 100 launches the application 114 that was used to author the embedded document and provides a live, editable version of the document, to the user. Accessing notebook 104 with the previews, receiving user selection of either a preview or the icon for the underlying document, and launching the corresponding application, are indicated by blocks 250, 252, and 254, in FIG. 4.

The application launched by notebook 100 receives the user's edits to the underlying document. This is indicated by block 256 in FIG. 4, and this can be done in a number of ways. For instance, the user may modify (such as add or delete or move) content within the underlying document. This is indicated by block 258. The user may also modify the relationship between pages in the document such that the previews should be reordered. For instance, if the underlying document is a spreadsheet document, and the user rearranges pages in the spreadsheet, then the order of the displayed previews for those pages should also be changed. User modification of the relationship between the previews is indicated by block 260 in FIG. 4. Similarly, the user may modify the dependency of the previews. For instance, if a spreadsheet document has a chart embedded on a page thereof, but the user wishes to give the chart its own page, then the dependency of the pages in the chart is changed. This also modifies the dependency of the previews generated for that document. Modifying the dependency in this way is indicated by block 262 in FIG. 4.

Figure 4A:
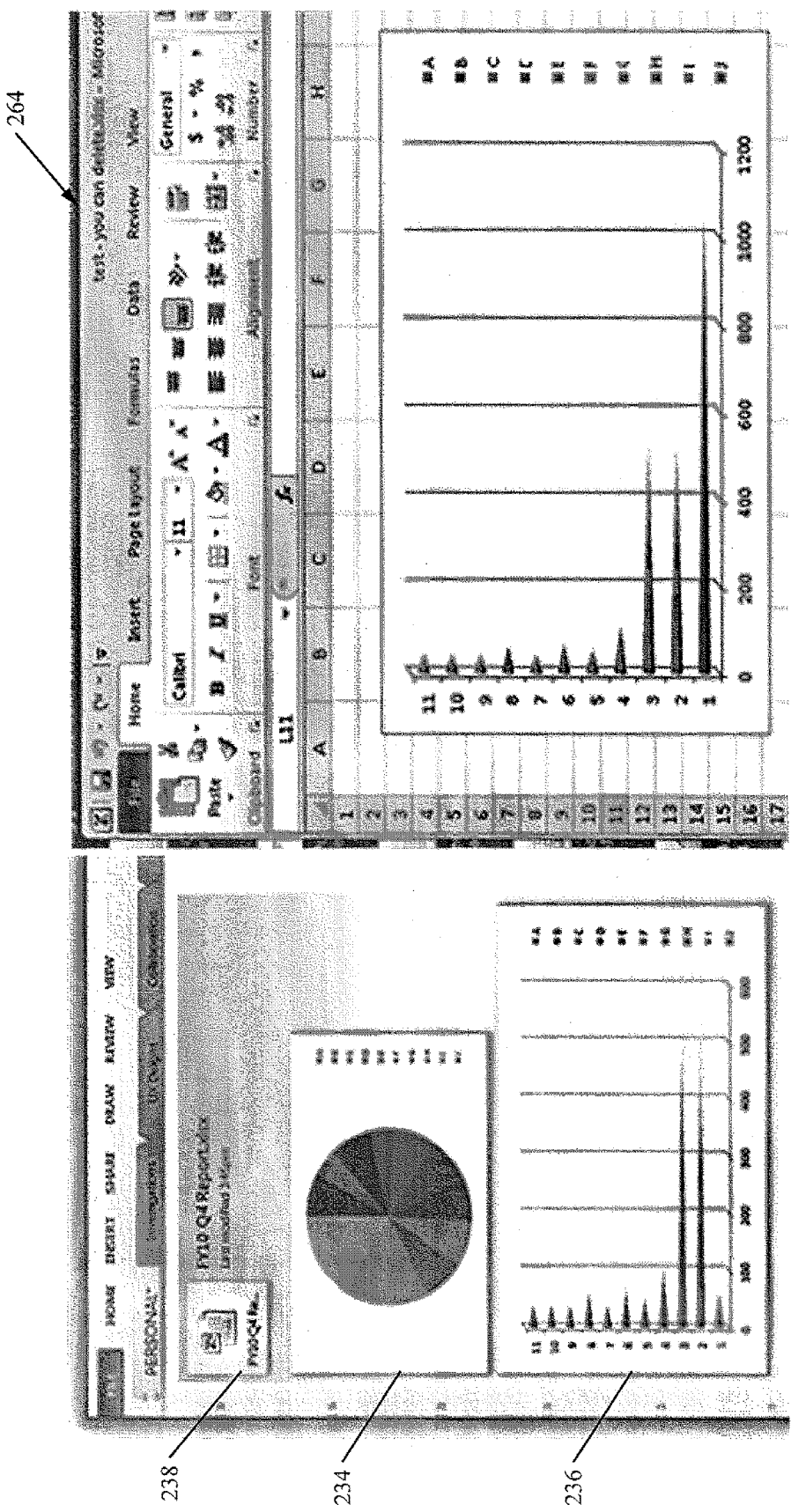
FIG. 4A shows one embodiment of an illustrative user interface display.

FIG. 4A shows one illustrative user interface 264 generated by user interface component 118, once a spreadsheet application 114 has been launched by the user clicking on preview 236. When this occurs, notebook system 110 launches the spreadsheet application 114, and navigates the user to the page in the spreadsheet application corresponding to preview 236. It can be seen on the right half of display 264 that the user has modified the graph corresponding to preview 236, in the underlying spreadsheet application. When the user saves the modifications to the spreadsheet document, this is detected by change detection component 122. Detecting the user saving the underlying document is indicated by block 266 in FIG. 4.

Preview generator 124 then determines whether changes need to be made to the previews 126 generated for the spreadsheet document displayed in FIG. 4A. In doing so, preview generator 124 accesses the saved implicit user preferences to determine which portions of the underlying document have had previews generated therefore. For instance, if the user has modified the underlying document, but has made modifications to a page that the user does not wish to be previewed, then no modifications to the previews 126 need to be made. However, if a page that is being previewed in notebook 104 has been modified in the underlying document, then that preview needs to be modified to reflect the content change made by the user. Accessing the implicit user preferences to determine whether the modifications require updating the previews 126 is indicated by block 268 in FIG. 4.

Preview generator 124 then updates the previews 126 corresponding to the embedded document based on the user edits or modifications to that document, and accounting for the implicit user preferences, as saved in content store 116. This is indicated by block 270 in FIG. 4.

To the extent that the previews 126 have been updated by preview generator 124, they are saved to notebook 104 in content store 116. This is indicated by block 272 in FIG. 4.

It may be that user 106 accesses the underlying document 112 which is embedded in notebook 104 and makes revisions to that document, without accessing the document through notebook 104. For instance, if the user separately opens up application 114 and navigates to the underlying document, the user may modify that document, without ever accessing the document through notebook 104, and without using notebook system 100. In that case, change detection component 122 may not detect the changes based on the modifications to the underlying document, and therefore preview generator 124 may not generate updated previews 126 for that document. This can be addressed using a manual refresh button.

Figure 5:
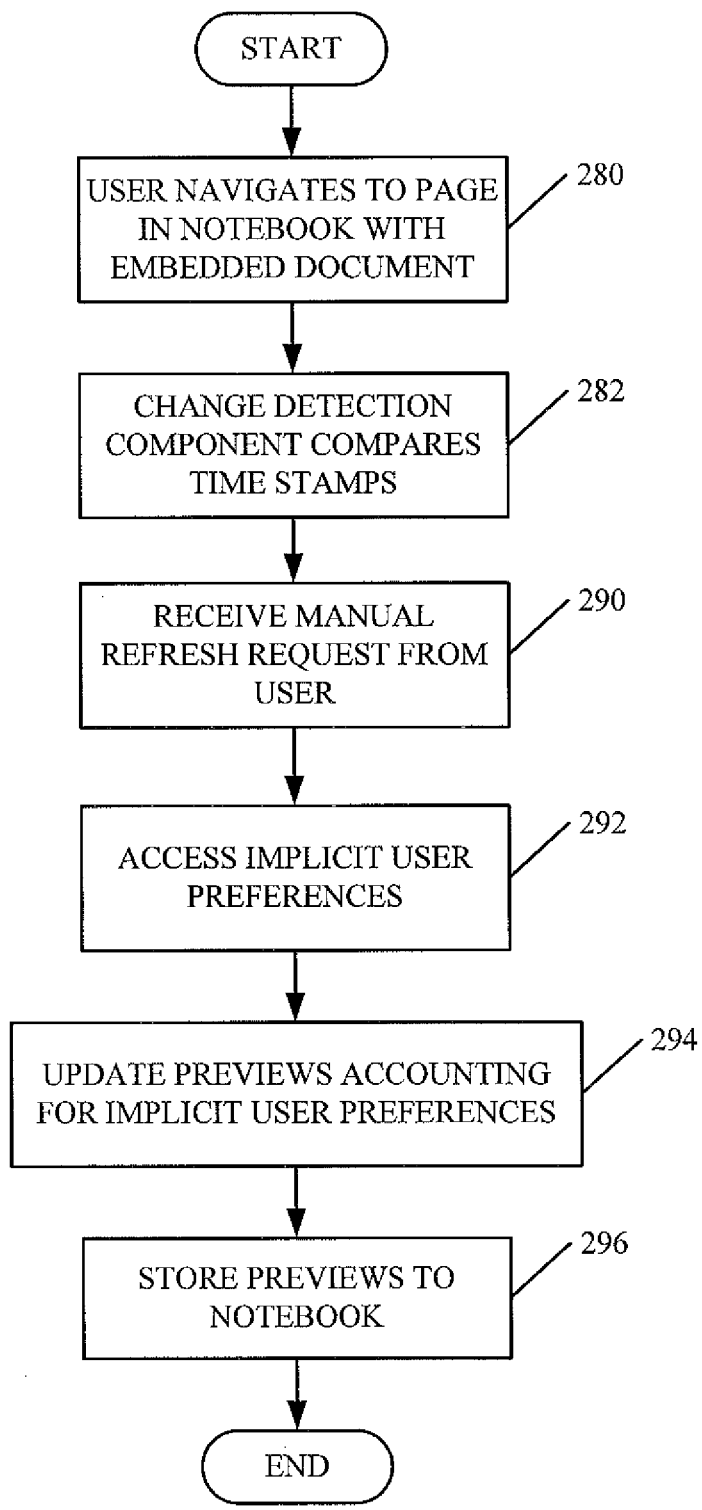
FIG. 5 is a flow diagram illustrating one embodiment of the operation of the system shown in FIG. 1 in performing a manual refresh of the preview objects.

FIG. 5 is a flow diagram illustrating one way that this can be done. With respect to FIG. 5, assume that user 106 has already made changes to the underlying document, without going through notebook system 100. Then, the user 106 goes through notebook system 100 and navigates to the page in notebook 104 that contains the embedded document. This is indicated by block 280 in FIG. 5. At that time, though the previews 126 for the embedded document will be displayed, this will not cause the application 114 to be launched, or to run. Therefore, change detection component 122 compares the time stamp on the data corresponding to the modified underlying document to the time stamp on the previously generated previews and displays an indicator that shows that the previews may be out of date. This is indicated by block 282 in FIG. 5.

Figure 5A:
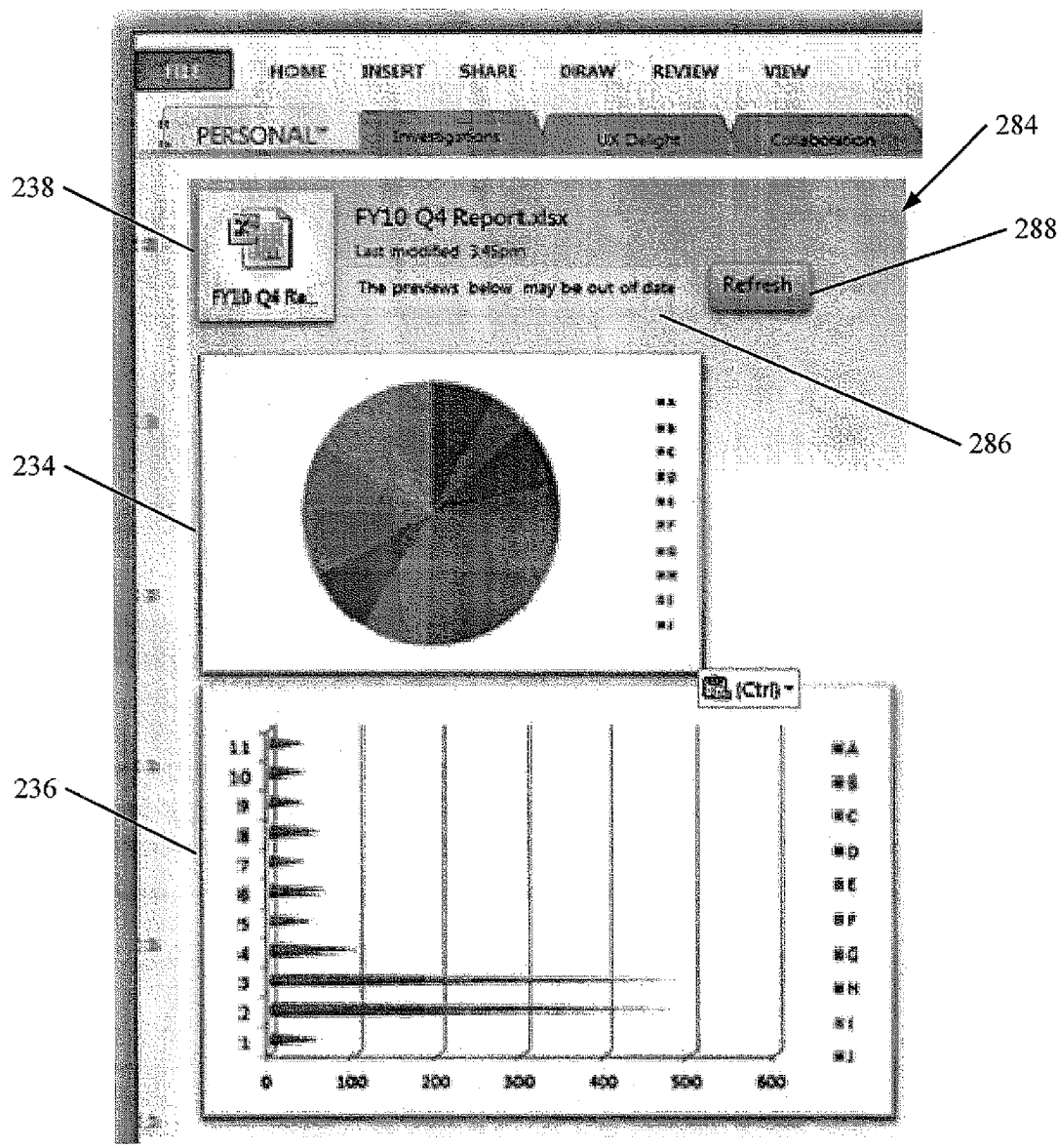
FIG. 5A shows one exemplary user interface display.

FIG. 5A shows a user interface display 284 that illustrates one way of doing this. For example, it can be seen that the user has navigated to the page in notebook 104 that contains the embedded file corresponding to icon 238. As change detection component 122 has compared the time stamp on the embedded file corresponding to icon 238 with those on the previews, change detection component 122 realizes, based on that comparison, that the currently displayed previews 126 (previews 234 and 236 in FIG. 5A) may be out of date. This message can be conveyed to the user, such as through a message in a text box 286, such as through a flashing icon, or in any other desired way.

When message 286 is generated, user interface component 118 may also illustratively generate a "Refresh" button 288 which is actuable by user 106. Seeing that the previews 126 may be out of date, user 126 can illustratively actuate button 288 by clicking on it or in any other desired way. This requests manual refresh of the previews for the underlying document. Receiving a manual refresh request from user 106 is indicated by block 290 in FIG. 5.

When this occurs, generator 124 accesses the implicit user preferences in content store 116 and updates previews 126 in the same way as described above. That is, the updates to the underlying document are made in the previews 126, accounting for the implicit user preferences, and the updated previews are again stored to notebook 104, in content store 116. This is indicated by blocks 292, 294 and 296 in FIG. 5.

Figure 6:
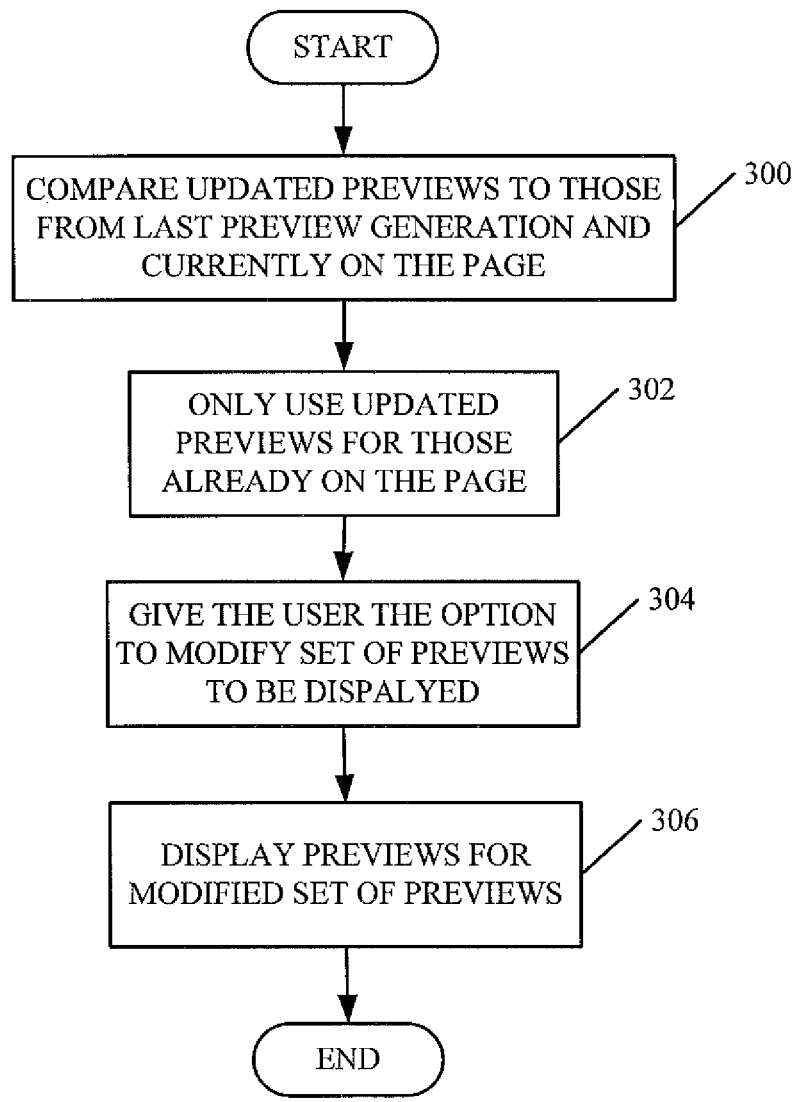
FIG. 6 is a flow diagram illustrating one embodiment of the system shown in FIG. 1 in modifying preview objects based on user modifications.

FIG. 6 is a flow diagram illustrating one way that preview generator 124 generates updated previews accounting for the stored user preferences. That is, if the user makes a change to the underlying document, but that page in the document is not being previewed, then preview generator 124 does not need to update previews 126 associated with this document. In order to determine this, preview generator 124 first compares the updated previews to those from the last preview generation as currently displayed on the given page of notebook 104. This is indicated by block 300 in FIG. 6. For instance, previews 234 and 236 are displayed on the page of the notebook, and preview generator 124 compares any updated previews to the previews 234 and 236 to determine whether the updated previews need to be displayed on the page of notebook 104 that contains the embedded document.

Preview generator 124 then only displays the updated previews for the previews that are already displayed on the page of notebook 104. That is, if either of the pages corresponding to previews 234 and 236 were modified, then the updated previews are used in place of the old previews. This is indicated by block 302 in FIG. 6.

In one embodiment, it may be that the user preference for the previews 126 may indicate that the user wants all pages of the document to be previewed (e.g., the user selected "Entire Spreadsheet" in FIG. 2H). Preview generator 124 can interpret this as the user wanting previews for all the current pages as well as any future pages added to the document. Therefore, change detection component 122 or content analyzer 120 notices that the user has added a new sheet to the spreadsheet document, preview generator 124 generates a corresponding preview 126 and inserts it into the desired page of notebook 104, in the proper order related to the other sheets. This can be an exception to the normal operation where the preview generator 124 only displays the updated previews for the previews that are already displayed on the page of notebook 104 and this logic is activated when the user preference indicates that s/he wanted to preview all pages of the document. On the other hand, if the user explicitly selected only certain pages or objects within the pages, or implicitly did this by deleting one or more previews (as explained above), the user preference is updated and is no longer "preview all the pages", in which case the preview generator 124 does not generate previews for new pages added to the document.

Also, in one embodiment, content analyzer 120 may exclude certain pages of the document if those pages do not have any content. For instance a spreadsheet may include several sheets, some of which may be empty. Content analyzer 120 will not consider these, and will not present them to the user as objects that are to be previewed, and preview generator 124 will not generate previews for them even if the user wanted to preview all the pages or the entire spreadsheet. These may also be pages that the user has marked to be hidden from external viewers in the application used to author the document. For instance a presentation may contain slides that are marked as "hidden", and therefore are not displayed during a slide show (e.g. pages that contain supplementary information that the author of the presentation did not want to display). Content analyzer 120 will illustratively exclude those pages in a similar way that it excludes pages with no content. If the user later adds content to these pages or removes the "hidden" marking, this change can be detected by change detection component 122 and previews 126 will be updated, assuming the user preference indicates that all pages should be previewed.

At any point in the process, preview generator 124 can again give the user the opportunity to modify the set of previews 126 to be displayed. This can be done, for instance, by again displaying the hierarchical tree structure, with a selection mechanism (such as check boxes) such as that shown at 174 in FIG. 2H. Of course, other ways of giving the user the option to modify the set of previews 126 to be displayed are contemplated herein as well, and this is indicated by block 304 in FIG. 6.

Finally, preview generator 124 generates the updated previews 126 and user interface component 118 displays the modified set of previews 126 on the given page in notebook 104. This is indicated by block 306 in FIG. 6.

The functionality of the items in FIG. 1 can be combined into fewer components or divided among other components as well. The items in FIG. 1 can also be deployed or consolidated among various devices. They can be deployed in a server-side architecture, a client-side architecture, split among different architectures or in a cloud computing environment.

Cloud computing provides computation, software, data access, and storage services that do not require end-user knowledge of the physical location or configuration of the system that delivers the services. In various embodiments, cloud computing delivers the services over a wide area network, such as the internet, using appropriate protocols.

For instance, cloud computing providers deliver applications over a wide area network and they can be accessed through a web browser or any other computing component. Software or components of the system in FIG. 1 as well as the corresponding data, can be stored on servers at a remote location. The computing resources in a cloud computing environment can be consolidated at a remote data center location or they can be dispersed. Cloud computing infrastructures can deliver services through shared data centers, even though they appear as a single point of access for the user. Thus, the components and functions described herein can be provided from a service provider at a remote location using a cloud computing architecture. Alternatively, they can be provided from a conventional server, or they can be installed on client devices directly, or in other ways.

Figure 7:
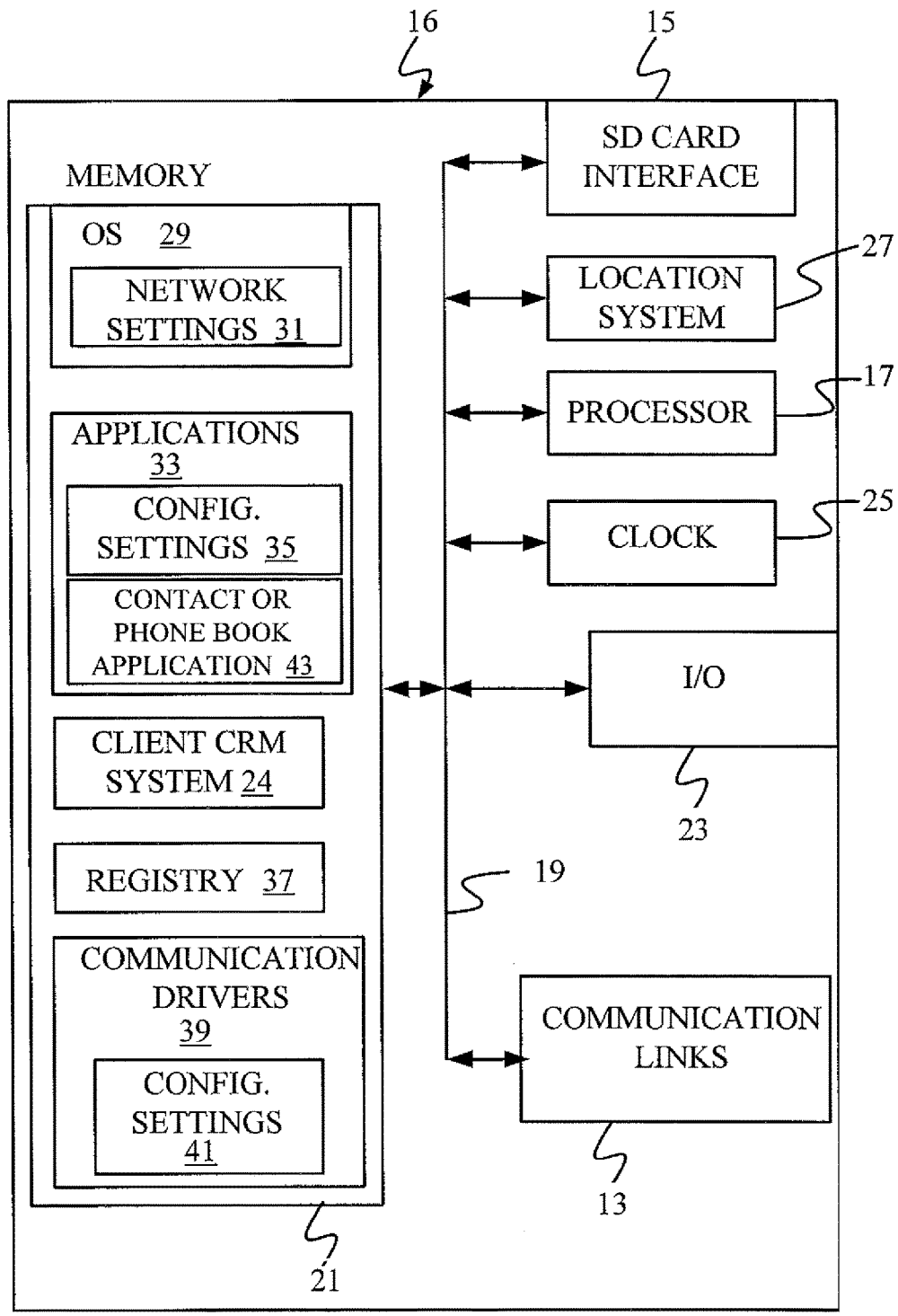
FIGS. 7-9 show various embodiments of mobile devices.
Figure 8:
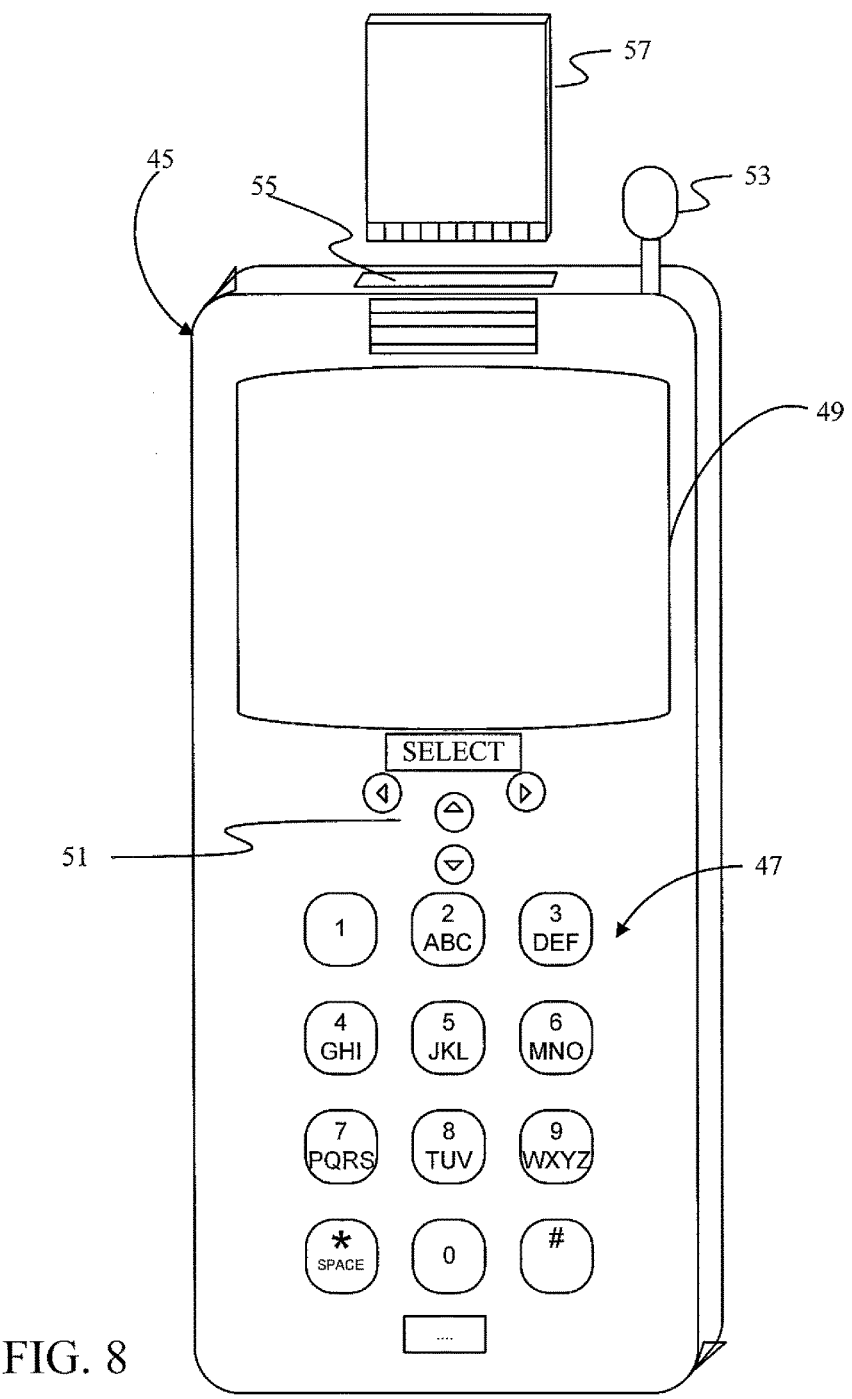
Figure 9:
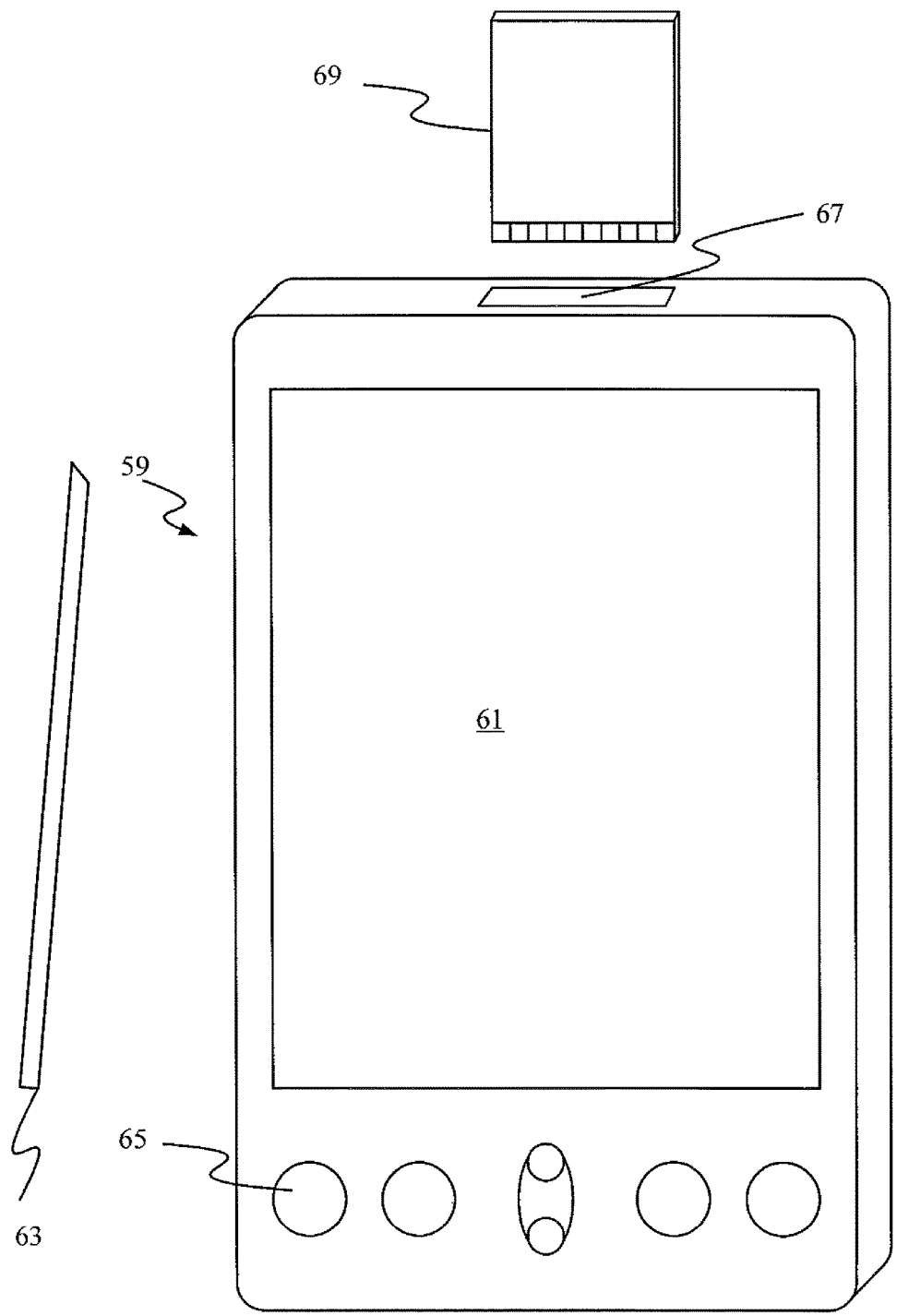

In any case, FIG. 7 is a simplified block diagram of one illustrative embodiment of a handheld or mobile computing device that can be used as a client device that user 106 uses to access system 100. Of course, some or all functionality of system 100 can be deployed on such a device as well. FIGS. 8 and 9 are examples of handheld or mobile devices.

FIG. 7 provides a general block diagram of the components of a client device that can run components of system 100 or that interacts with system 100, or both. In the device 16, a communications link 13 is provided that allows the handheld device to communicate with other computing devices and under some embodiments provides a channel for receiving information automatically, such as by scanning. Examples of communications link 13 include an infrared port, a serial/USB port, a cable network port such as an Ethernet port, and a wireless network port allowing communication though one or more communication protocols including General Packet Radio Service (GPRS), 1Xrtt, and Short Message Service, which are wireless services used to provide cellular access to a network, as well as 802.11 and 802.11b (Wi-Fi) protocols, and Bluetooth protocol, which provide local wireless connections to networks.

Under other embodiments, applications or systems (like system 10) are received on a removable Secure Digital (SD) card that is connected to a SD card interface 15. SD card interface 15 and communication links 13 communicate with a processor 17 (which can also embody processor 125 from FIG. 1) along a bus 19 that is also connected to memory 21 and input/output (I/O) components 23, as well as clock 25 and location system 27.

I/O components 23, in one embodiment, are provided to facilitate input and output operations. I/O components 23 for various embodiments of the device 16 can include input components such as buttons, touch sensors, touch screens, proximity sensors, microphones, tilt sensors, and gravity switches and output components such as a display device, a speaker, and or a printer port. Other I/O components 23 can be used as well.

Clock 25 illustratively comprises a real time clock component that outputs a time and date. It can also, illustratively, provide timing functions for processor 17.

Location system 27 illustratively includes a component that outputs a current geographical location of device 16. This can include, for instance, a global positioning system (GPS) receiver, a LORAN system, a dead reckoning system, a cellular triangulation system, or other positioning system. It can also include, for example, mapping software or navigation software that generates desired maps, navigation routes and other geographic functions.

Memory 21 stores operating system 29, network settings 31, applications 33, application configuration settings 35, registry 37, communication drivers 39, and communication configuration settings 41. Memory 21 can include all types of tangible volatile and non-volatile computer-readable memory devices. It can also include computer storage media (described below). Memory 21 stores computer readable instructions that, when executed by processor 17, cause the processor to perform computer-implemented steps or functions according to the instructions. System 100 or the items in data store 116, for example, can reside in memory 21. Processor 17 can be activated by other components to facilitate their functionality as well.

Examples of the network settings 31 include things such as proxy information, Internet connection information, and mappings. Application configuration settings 35 include settings that tailor the application for a specific enterprise or user. Communication configuration settings 41 provide parameters for communicating with other computers and include items such as GPRS parameters, SMS parameters, connection user names and passwords.

Applications 33 can be applications that have previously been stored on the device 16 or applications that are installed during use, although these can be part of operating system 29, or hosted external to device 16, as well.

FIGS. 8 and 9 provide examples of devices 16 that can be used, although others can be used as well. In FIG. 8, a smart phone or mobile phone 45 is provided as the device 16. Phone 45 includes a set of keypads 47 for dialing phone numbers, a display 49 capable of displaying images including application images, icons, web pages, photographs, and video, and control buttons 51 for selecting items shown on the display. The phone includes an antenna 53 for receiving cellular phone signals such as General Packet Radio Service (GPRS) and 1Xrtt, and Short Message Service (SMS) signals. In some embodiments, phone 45 also includes a Secure Digital (SD) card slot 55 that accepts a SD card 57.

The mobile device of FIG. 9 is a personal digital assistant (PDA) 59 or a multimedia player or a tablet computing device, etc. (hereinafter referred to as PDA 59). PDA 59 includes an inductive screen 61 that senses the position of a stylus 63 (or other pointers, such as a user's finger) when the stylus is positioned over the screen. This allows the user to select, highlight, and move items on the screen as well as draw and write. PDA 59 also includes a number of user input keys or buttons (such as button 65) which allow the user to scroll through menu options or other display options which are displayed on display 61, and allow the user to change applications or select user input functions, without contacting display 61. Although not shown, PDA 59 can include an internal antenna and an infrared transmitter/receiver that allow for wireless communication with other computers as well as connection ports that allow for hardware connections to other computing devices. Such hardware connections are typically made through a cradle that connects to the other computer through a serial or USB port. As such, these connections are non-network connections. In one embodiment, mobile device 59 also includes a SD card slot 67 that accepts a SD card 69.

Note that other forms of the devices 16 are possible. Examples include tablet computing devices, music or video players, and other handheld computing devices.

Figure 10:
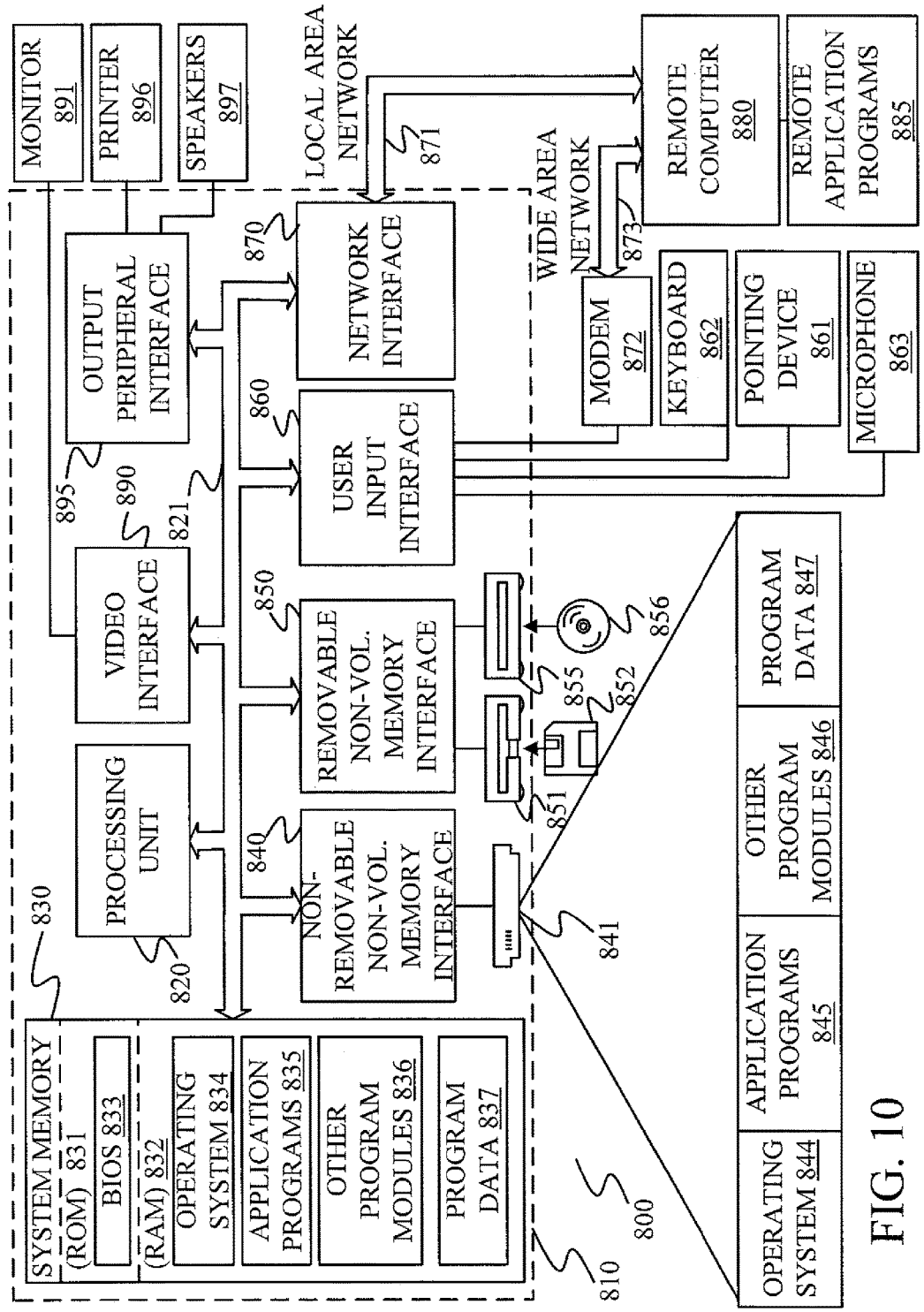
FIG. 10 shows a block diagram of one illustrative computing environment.

FIG. 10 is one embodiment of a computing environment in which system 100 (for example) can be deployed. With reference to FIG. 10, an exemplary system for implementing some embodiments includes a general-purpose computing device in the form of a computer 810. Components of computer 810 may include, but are not limited to, a processing unit 820 (which can comprise processor 125) a system memory 830, and a system bus 821 that couples various system components including the system memory to the processing unit 820. The system bus 821 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus. Memory and programs described with respect to FIG. 1 can be deployed in corresponding portions of FIG. 10.

Computer 810 typically includes a variety of computer readable media. Computer readable media can be any available media that can be accessed by computer 810 and includes both volatile and nonvolatile media, removable and non-removable media. By way of example, and not limitation, computer readable media may comprise computer storage media and communication media. Computer storage media is different from, and does not include, a modulated data signal or carrier wave. It includes hardware storage media including both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by computer 810. Communication media typically embodies computer readable instructions, data structures, program modules or other data in a transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

The system memory 830 includes computer storage media in the form of volatile and/or nonvolatile memory such as read only memory (ROM) 831 and random access memory (RAM) 832. A basic input/output system 833 (BIOS), containing the basic routines that help to transfer information between elements within computer 810, such as during start-up, is typically stored in ROM 831. RAM 832 typically contains data and/or program modules that are immediately accessible to and/or presently being operated on by processing unit 820. By way of example, and not limitation, FIG. 10 illustrates operating system 834, application programs 835, other program modules 836, and program data 837.

The computer 810 may also include other removable/non-removable volatile/nonvolatile computer storage media. By way of example only, FIG. 10 illustrates a hard disk drive 841 that reads from or writes to non-removable, nonvolatile magnetic media, a magnetic disk drive 851 that reads from or writes to a removable, nonvolatile magnetic disk 852, and an optical disk drive 855 that reads from or writes to a removable, nonvolatile optical disk 856 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 841 is typically connected to the system bus 821 through a non-removable memory interface such as interface 840, and magnetic disk drive 851 and optical disk drive 855 are typically connected to the system bus 821 by a removable memory interface, such as interface 850.

The drives and their associated computer storage media discussed above and illustrated in FIG. 10, provide storage of computer readable instructions, data structures, program modules and other data for the computer 810. In FIG. 10, for example, hard disk drive 841 is illustrated as storing operating system 844, application programs 845, other program modules 846, and program data 847. Note that these components can either be the same as or different from operating system 834, application programs 835, other program modules 836, and program data 837. Operating system 844, application programs 845, other program modules 846, and program data 847 are given different numbers here to illustrate that, at a minimum, they are different copies.

A user may enter commands and information into the computer 810 through input devices such as a keyboard 862, a microphone 863, and a pointing device 861, such as a mouse, trackball or touch pad. Other input devices (not shown) may include a joystick, game pad, satellite dish, scanner, or the like. These and other input devices are often connected to the processing unit 820 through a user input interface 860 that is coupled to the system bus, but may be connected by other interface and bus structures, such as a parallel port, game port or a universal serial bus (USB). A monitor 891 or other type of display device is also connected to the system bus 821 via an interface, such as a video interface 890. In addition to the monitor, computers may also include other peripheral output devices such as speakers 897 and printer 896, which may be connected through an output peripheral interface 895.

The computer 810 is operated in a networked environment using logical connections to one or more remote computers, such as a remote computer 880. The remote computer 880 may be a personal computer, a hand-held device, a server, a router, a network PC, a peer device or other common network node, and typically includes many or all of the elements described above relative to the computer 810. The logical connections depicted in FIG. 10 include a local area network (LAN) 871 and a wide area network (WAN) 873, but may also include other networks. Such networking environments are commonplace in offices, enterprise-wide computer networks, intranets and the Internet.

When used in a LAN networking environment, the computer 810 is connected to the LAN 871 through a network interface or adapter 870. When used in a WAN networking environment, the computer 810 typically includes a modem 872 or other means for establishing communications over the WAN 873, such as the Internet. The modem 872, which may be internal or external, may be connected to the system bus 821 via the user input interface 860, or other appropriate mechanism. In a networked environment, program modules depicted relative to the computer 810, or portions thereof, may be stored in the remote memory storage device. By way of example, and not limitation, FIG. 10 illustrates remote application programs 885 as residing on remote computer 880. It will be appreciated that the network connections shown are exemplary and other means of establishing a communications link between the computers may be used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A computer-implemented method of processing a document in a notebook system, comprising:
   receiving, by a notebook system, a document to be represented in a notebook in the notebook system, the document being separate from the notebook;
   selecting, by the notebook system, items in the document for which to generate a preview;
   generating, by the notebook system, a set of one or more previews, each preview corresponding to one of the selected items in the document;
   generating a notebook display that displays a notebook page of the notebook and includes the set of previews, each preview being generated and displayable in the notebook display without an application used to author the document being launched;
   receiving an indication of a modification input;
   based on the modification input, modifying, by the notebook system, the set of previews without the application used to author the document being launched; and
   updating, by the notebook system, the notebook display to include the modified set of previews.

2. The computer-implemented method of claim 1, wherein receiving an indication of a modification input comprises:
   receiving a user modification input directly interacting with the set of previews, wherein the set of previews are modified based on the user modification input without launching the application used to author the document.

3. The computer-implemented method of claim 2 wherein modifying the set of previews comprises:
   deleting one or more previews from the set of previews based on the user modification input.

4. The computer-implemented method of claim 2, wherein the set of previews comprises a plurality of previews, and wherein modifying the set of previews comprises:
   reordering one or more previews in the set of previews based on the user modification input.

5. The computer-implemented method of claim 1, and further comprising:
   receiving user selection of a particular one of the previews;
   in response to the user selection, launching the application used to author the document; and
   opening the document in the application.

6. The computer-implemented method of claim 5 wherein opening the document in the application comprises:
   navigating the user to an item in the document for which the selected preview was generated.

7. The computer-implemented method of claim 1, wherein the document comprises a plurality of document items and the set of previews comprises a plurality of previews, each of the previews corresponding to one the document items, and wherein the modification to the document comprises a re-ordering of the plurality of document items within the document, and wherein modifying the set of previews comprises:
   re-ordering the plurality of previews on the notebook page based on the re-ordering of the plurality of document items.

8. The computer-implemented method of claim 1, wherein receiving an indication of a modification input comprises:
   receiving the modification input from the application, the modification input being indication of a modification to the document using the application, wherein modifying the set of previews comprises automatically modifying the set of previews based on the indication modification to the document.

9. The computer-implemented method of claim 8, wherein the modification to the document comprises deleting a document item from the document, the document item having a corresponding preview in the set of previews, and wherein automatically modifying the set of previews comprises:
   automatically deleting the corresponding preview from the set of previews on the notebook page.

10. The computer-implemented method of claim 8, wherein the modification to the document comprises a modification to content of a document item in the document, the document item having a corresponding preview in the set of previews, and wherein automatically modifying the set of previews comprises:
    automatically synchronizing the set of previews with the document to update the corresponding preview based on the modification to the content of the document item.

11. The computer-implemented method of claim 8, the modification to the document comprises adding a new document item to the document, and wherein automatically modifying the set of previews comprises:
    automatically adding a new preview to the set of previews on the notebook page, the new preview corresponding to the new document item.

12. The computer-implemented method of claim 11, wherein selecting items in the document comprises:
    enumerating items in the document for which a preview can be generated;
    receiving a user selection of the enumerated items; and
    generating a preview object for each of the selected items.

13. The computer-implemented method of claim 12 wherein enumerating items comprises:
    identifying a hierarchical structure of items in the document; and
    generating a hierarchical display displaying hierarchical structure of items for user selection.

14. The computer-implemented method of claim 13 wherein generating the hierarchical display comprises displaying the hierarchical structure of items having at least one node with at least one child node dependent from the at least one node, and wherein identifying a hierarchical structure comprises:
    accessing an object model corresponding to the application used to author the document; and
    analyzing the document using the object model to identify the hierarchical structure of items.

15. The computer-implemented method of claim 14 wherein the hierarchical structure of items displayed to the user in the hierarchical display comprises a selectable element associated with each node and each child node, and wherein user selection of the selectable item associated with a given node causes automatic selection of all child nodes dependent from the given node.

16. The computer-implemented method of claim 13 wherein the hierarchical structure depicts a flat hierarchy of items in which all nodes at a same level of the hierarchical structure.

17. The computer-implemented method of claim 1 and further comprising:
saving the modified set of previews for subsequent display to the user.

18. A notebook system, comprising:
a content analyzer configured to receive a document, that is separate from a notebook, for introduction into a notebook page of the notebook, access a model corresponding to an application used to author the document, and analyze the document, based on the model, to identify a hierarchical structure of items in the document;
a user interface component configured to display the hierarchical structure of items for user selection, and to receive a user selection of a set of the items from the displayed hierarchical structure, the set of items comprising a plurality of different items in the document;
a preview generator configured to generate a plurality of previews, each preview in the plurality of previews corresponding to an item in the set of items, the user interface component being configured to display the plurality of previews when a user accesses the notebook page;
a change detection component configured to detect a user modification to a relationship between various previews in the plurality of previews, the preview generator being configured to generate modified previews, using a computer processor, to indicate the user modification, and the user interface component being configured to display the modified previews when the user next accesses the notebook page.

19. A computer-implemented method of processing a document in a notebook system, comprising:
receiving a document that is separate from a notebook in the notebook system;
enumerating items in the document for which a preview can be generated by accessing a model corresponding to the application used to author the document, and identifying a hierarchical structure of items in the document using the model, wherein the model models a document structure of the document;
displaying the hierarchical structure of items having at least one node with at least one child node dependent from the at least one node and a selectable element associated with each node and each child node, user selection of the selectable item associated with a given node causing automatic selection of all child nodes dependent from the given node;
receiving a selection of at least one node or child node in the hierarchical structure of items;
generating a preview object for each of the selected nodes or child nodes;
generating a notebook display that displays the notebook with the preview objects, the preview objects being displayable in the notebook display, regardless of whether the application used to author the document is launched;
receiving a user modification input modifying the plurality of previews;
updating the notebook display to display the modified set of previews; and
saving the modified set of previews for subsequent display to the user.

20. The computer-implemented method of claim 19, wherein receiving a selection comprises receiving a selection of a plurality of nodes in the hierarchical structure of items, and generating the notebook display comprises generating a set of preview objects corresponding to the document, wherein each preview object comprises a preview of a selected item, selected based on the selection of the plurality of nodes.

* * * * *